US007250198B2

(12) United States Patent
Heckmeier et al.

(10) Patent No.: US 7,250,198 B2

(45) **Date of Patent: *Jul. 31, 2007**

(54) LIQUID-CRYSTALLINE COMPOUNDS

(75) Inventors: Michael Heckmeier, Bensheim (DE); Peer Kirsch, Darmstadt (DE); Joachim Krause, Dieburg (DE); Alexander Hahn, Rüsselsheim (DE); Andreas Ruhl, Rossdorf (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/259,795

(22) Filed: Sep. 30, 2002

(65) Prior Publication Data

US 2003/0213935 A1 Nov. 20, 2003

(30) Foreign Application Priority Data

Sep. 29, 2001 (DE) ................................ 101 48 356

(51) Int. Cl.

*C09K 19/34* (2006.01)
*C09K 19/32* (2006.01)
*C09K 19/30* (2006.01)
*C09K 19/12* (2006.01)
*C09K 19/20* (2006.01)

(52) U.S. Cl. ............. 428/1.1; 252/299.61; 252/299.62; 252/299.63; 252/299.66; 252/299.67

(58) Field of Classification Search ........... 252/299.61, 252/299.63, 299.66, 299.67, 299.62; 570/127, 570/129, 130, 131; 428/1.1

See application file for complete search history.

(56) References Cited

U.S. PATENT DOCUMENTS 5,858,270 A * 1/1999 Matsui et al. .......... 252/299.01
6,007,740 A * 12/1999 Andou et al. .......... 252/299.63
6,162,372 A * 12/2000 Tomi et al. .............. 252/299.6
6,630,210 B2 * 10/2003 Kirsch et al. ................ 428/1.1
6,723,866 B2 * 4/2004 Kirsch et al. ................. 558/17
6,908,645 B2 * 6/2005 Kirsch et al. ................ 428/1.1
6,962,733 B2 * 11/2005 Heckmeier et al. .......... 428/1.1
6,964,794 B2 * 11/2005 Heckmeier et al. .......... 428/1.1
7,001,646 B2 * 2/2006 Heckmeier et al. .......... 428/1.1
7,105,210 B2 * 9/2006 Heckmeier et al. .......... 428/1.1

FOREIGN PATENT DOCUMENTS

DE 19961702 * 6/2001

* cited by examiner

*Primary Examiner*—Shean C Wu

(74) *Attorney, Agent, or Firm*—Millen, White, Zelano & Branigan, P.C.

(57) ABSTRACT

Liquid-crystalline compounds of the formula I

I

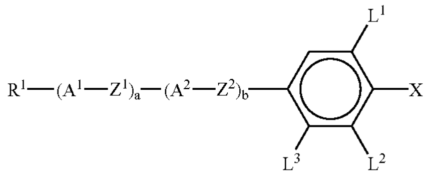

in which $R^1$, $A^1$, $A^2$, $Z^1$, $Z^2$, X, a, b, $L^1$, $L^2$ and $L^3$ are as defined herein, and to liquid-crystalline media comprising at least one compound of the formula I and to electro-optical displays containing a liquid-crystalline medium of this type.

17 Claims, No Drawings

LIQUID-CRYSTALLINE COMPOUNDS

The present invention relates to liquid-crystalline compounds and to a liquid-crystalline medium, to the use thereof for electro-optical purposes, and to displays containing this medium.

Liquid-crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (super-birefringence effect) cells and OMI (optical mode interference) cells. The most common display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and low vapor pressure are desired.

Matrix liquid-crystal displays of this type are known. Non-linear elements which can be used for individual switching of the individual pixels are, for example, active elements (i.e. transistors). The term “active matrix” is then used, where a distinction can be made between two types:

1. MOS (metal oxide semiconductor) or other diodes on a silicon wafer as substrate.
2. Thin-film transistors (TFTs) on a glass plate as substrate.

The use of single-crystal silicon as substrate material restricts the display size, since even modular assembly of various part-displays results in problems at the joins.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully color-capable displays, in which a mosaic of red, green and blue filters is arranged in such a way that a filter element is opposite each switchable pixel.

The TFT displays usually operate as TN cells with crossed polarizers in transmission and are illuminated from the back.

The term MLC displays here covers any matrix display with integrated non-linear elements, i.e., besides the active matrix, also displays with passive elements, such as varistors or diodes (MIM=metal-insulator-metal).

MLC displays of this type are particularly suitable for TV applications (for example pocket TVs) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable service lives. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not meet today’s requirements.

There thus continues to be a great demand for MLC displays having very high specific resistance at the same time as a large working-temperature range, short response times even at low temperatures and low threshold voltage which do not have these disadvantages, or only do so to a reduced extent.

In TN (Schadt-Helfrich) cells, media are desired which facilitate the following advantages in the cells:

- extended nematic phase range (in particular down to low temperatures)
- the ability to switch at extremely low temperatures (outdoor use, automobile, avionics)
- increased resistance to UV radiation (longer service life)
- high $\Delta n$ for faster response times The media available from the prior art do not allow these advantages to be achieved while simultaneously retaining the other parameters.

In the case of supertwisted (STN) cells, media are desired which enable greater multiplexability and/or lower threshold voltages and/or broader nematic phase ranges (in particular at low temperatures). To this end, a further widening of the available parameter latitude (clearing point, smectic-nematic transition or melting point, viscosity, dielectric parameters, elastic parameters) is urgently desired.

The invention has an object of providing media, in particular for MLC, IPS, TN or STN displays of this type, which do not have the above-mentioned disadvantages or only do so to a reduced extent, and preferably simultaneously have very high specific resistances and low threshold voltages. This object requires liquid-crystalline compounds which have a high clearing point and low rotational viscosity.

Upon further study of the specification and appended claims, further objects and advantages of this invention will become apparent to those skilled in the art.

It has now been found that these objects and others can be achieved if the liquid-crystalline compounds according to the invention are used.

The invention thus relates to liquid-crystalline compounds of the formula I

I

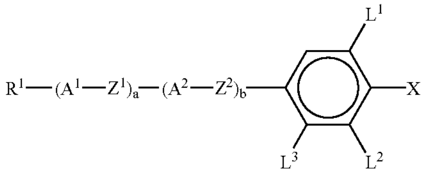

in which

R is H, an alkenyl radical having from 2 to 15 carbon atoms which is unsubstituted, monosubstituted by CN or $CF_3$ or at least monosubstituted by halogen, where, in addition, one or more $CH_2$ groups in these radicals may be replaced by —O—, —S—, —CH═CH—, —C≡C—, —OC—O— or —O—CO— in such a way that O atoms are not linked directly to one another, $A^1$ and $A^2$ are each, independently of one another, a) a 1,4-cyclohexenylene or 1,4-cyclohexylene radical, in which one or two non-adjacent $CH_2$ groups may be replaced by —O— or —S—, b) a 1,4-phenylene radical, in which one or two CH groups may be replaced by N, c) a radical from the group consisting of piperidine-1,4-diyl, 1,4-bicyclo[2.2.2]octylene, phenanthrene-2,7-diyl, naphthalene-2,6-diyl, decahydronaphthalene-2,6-diyl, 1,2,3,4-tetrahydronaphthalene-2,6-diyl, phenanthrene-2,7-diyl and fluorene-2,7-diyl, where the radicals a), b) and c) may be monosubstituted or polysubstituted by halogen atoms, X is F, Cl, CN, NCS, $SF_5$, or a halogenated or unsubstituted alkyl, alkoxy, alkenyloxy or alkenyl radical having up to 5 carbon atoms, $Z^1$ and $Z^2$ are each, independently of one another, —CO—O—, —O—CO—, —$CF_2$O—, —O$CF_2$—, —$CH_2$O—, —O$CH_2$—, —$CH_2CH_2$—, —$(CH_2)_4$—, —$C_2F_4$—, —$CH_2CF_2$—, —$CF_2CH_2$—, —CF═CF—, —CH═CH—, —C≡C— or a single bond, with the proviso that at least one of the bridges $Z^1$ and $Z^2$ is —$CF_2$O— or —O$CF_2$—, a is 0, 1 or 2, b is 0, 1 or 2, and $L^1$, $L^2$ and $L^3$ are each, independently of one another, H, F or Cl.

The invention furthermore relates to the use of the compounds of the formula I in liquid-crystalline media.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or in order to optimize its threshold voltage and/or its viscosity.

In the pure state, the compounds of the formula I are colorless and form liquid-crystalline mesophases in a temperature range which is favorably located for electro-optical use. In particular, the compounds according to the invention are distinguished by their broad nematic phase range. In liquid-crystalline mixtures, the substances according to the invention suppress the smectic phases and result in a clear improvement in the low-temperature storage stability. They are stable chemically, thermally and to light.

The invention relates in particular to the compounds of the formula I in which R is vinyl, $CH_3CH$═CH, $CH_2$═$CHCH_2CH_2$ or $CH_3CH_2$═$CHCH_2CH_2$.

Particular preference is given to compounds of the formula I in which a=b=1 or a=b=2. $Z^1$ or $Z^2$ is preferably a single bond, furthermore —$CF_2$O—, —O$CF_2$—, —$C_2F_4$—, —$CH_2$O—, —O$CH_2$— or —COO—.

The alkenyl radical R may be straight-chain or branched. It is preferably straight-chain and has from 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, 4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkenyl radical which is monosubstituted by CN or $CF_3$, this radical is preferably straight-chain. The substitution by CN or $CF_3$ is, in any desired position.

If R is an alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Compounds of the formula I containing branched wing groups R may occasionally be of importance owing to better solubility in the conventional liquid-crystalline base materials, but in particular as chiral dopants if they are optically active. Smectic compounds of this type are suitable as components of ferroelectric materials.

Compounds of the formula I having $S_A$ phases are suitable for thermally addressed displays.

For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical, Bi denotes a bicyclo[2.2.2]octylene radical, PheF denotes a 2- or 3-fluoro-1,4-phenylene radical, PheFF denotes a 2,3-difluoro- or 2,6-difluoro-1,4-phenylene radical, Nap denotes a substituted or unsubstituted naphthalene radical, Dec denotes a decahydronaphthalene radical, and Phen denotes a substituted or unsubstituted phenanthrene radical.

For reasons of simplicity, $A^3$—X below denotes

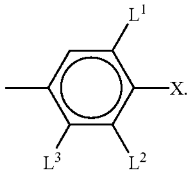

The compounds of the formula I accordingly include the preferred bicyclic compounds of the sub-formulae Ia to Ij:

($Z^2$=—$CF_2O$— or —$OCF_2$—):

| | |
|---|---|
| R-Cyc-$Z^2$-$A^3$-X | Ia |
| R-Phe-$Z^2$-$A^3$-X | Ib |
| R-Pyr-$Z^2$-$A^3$-X | Ic |
| R-Dio-$Z^2$-$A^3$-X | Id |
| R-Bi-$Z^2$-$A^3$-X | Ie |
| R-PheF-$Z^2$-$A^3$-X | If |
| R-PheFF-$Z^2$-$A^3$-X | Ig |
| R-Nap-$Z^2$-$A^3$-X | Ih |
| R-Dec-$Z^2$-$A^3$-X | Ii |
| R-Phen-$Z^2$-$A^3$-X | Ij |

The compounds of the formula I accordingly include the preferred tricyclic compounds of the sub-formulae Ik to Iv:

($Z^1$ or $Z^2$: —$CF_2O$— or —$OCF_2$—):

| | |
|---|---|
| R-Cyc-$Z^1$-Cyc-$Z^2$-$A^3$-X | Ik |
| R-Cyc-$Z^1$-Phe-$Z^2$-$A^3$-X | Il |
| R-Cyc-$Z^1$-PheF-$Z^2$-$A^3$-X | Im |
| R-Cyc-$Z^1$-PheFF-$Z^2$-$A^3$-X | In |
| R-Phe-$Z^1$-Phe-$Z^2$-$A^3$-X | Io |
| R-Cyc-$Z^1$-Dio-$Z^2$-$A^3$-X | Ip |
| R-Dio-$Z^1$-Cyc-$Z^2$-$A^3$-X | Iq |
| R-Dec-$Z^1$-Cyc-$Z^2$-$A^3$-X | Ir |
| R-Phe-$Z^1$-PheF-$Z^2$-$A^3$-X | Is |
| R-Phe-$Z^1$-PheFF-$Z^2$-$A^3$-X | It |
| R-Pyr-$Z^1$-Phe-$Z^2$-$A^3$-X | Iu |
| R-Phe-$Z^1$-Phen-$Z^2$-$A^3$-X | Iv |

Of these, particular preference is given to the compounds of the sub-formulae Ia, Ib, Id, Ik, and Il.

$A^1$ and $A^2$ are preferably Phe, PheF, PheFF, Cyc or Che, furthermore Pyr or Dio, Dec or Nap. The compounds of the formula I preferably contain not more than one of the radicals Bi, Pyd, Pyr, Dio, Dit, Nap or Dec.

Preference is also given to all compounds of the formula I and of all sub-formulae in which $A^1$ and $A^2$ are a mono-substituted or disubstituted 1,4-phenylene. These are, in particular, 2-fluoro-1,4-phenylene, 3-fluoro-1,4-phenylene, 2,3-difluoro-1,4-phenylene and 2,6-difluoro-1,4-phenylene.

Preferred subgeneric groups of compounds of the formula I are those of the sub-formulae I1 to I105:

I1

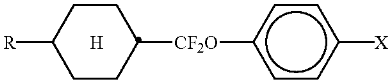

-continued

I2

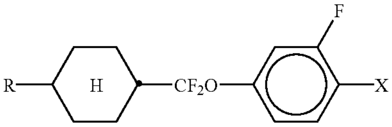

I3

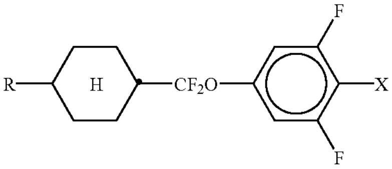

I4

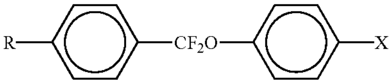

I5

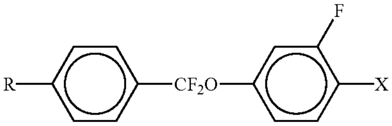

I6

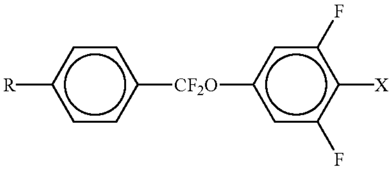

I7

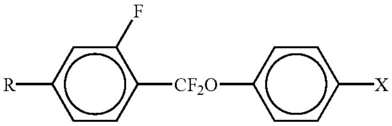

I8

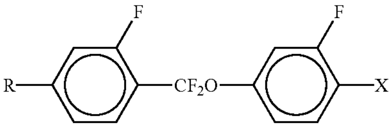

I9

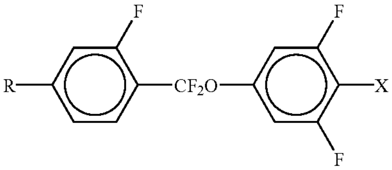

I10

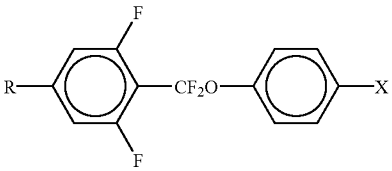

I11

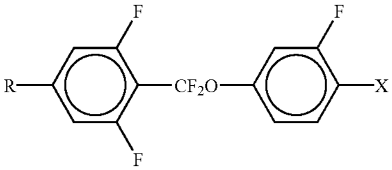

-continued
I12
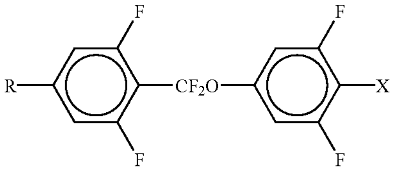
I13
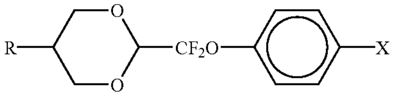
I14
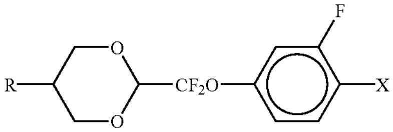
I15
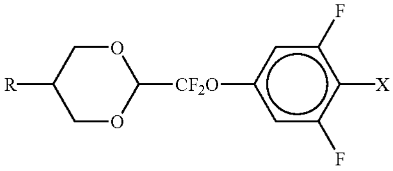
I16
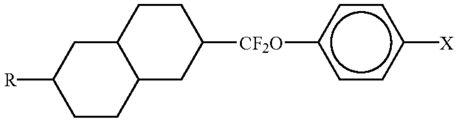
I17
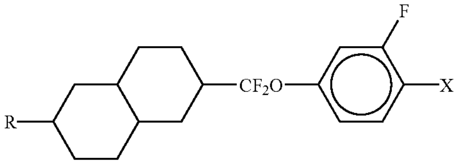
I18
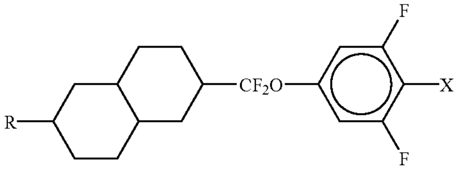
I19
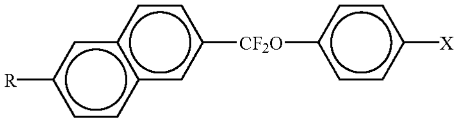
I20
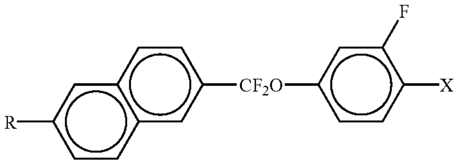
I21
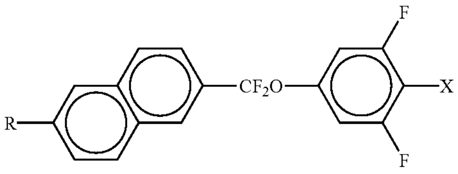
-continued
I22
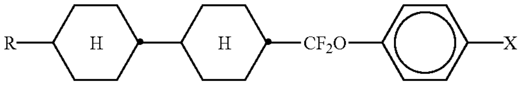
I23
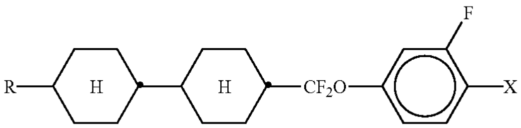
I24
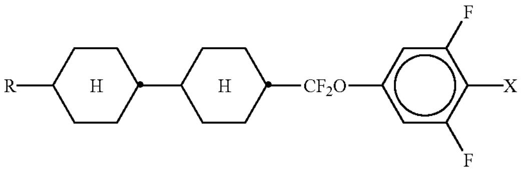
I25
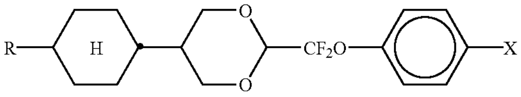
I26
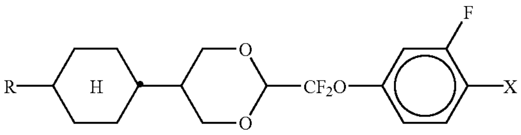
I27
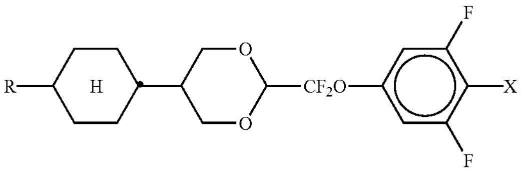
I28
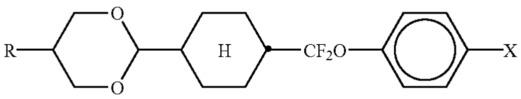
I29
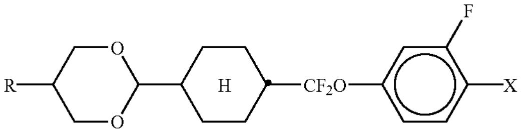
I30
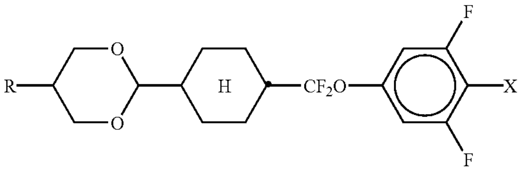
I31
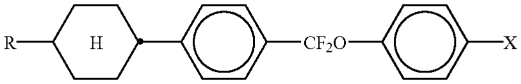

-continued
I32
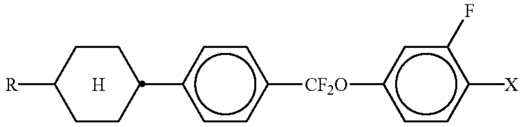
I33
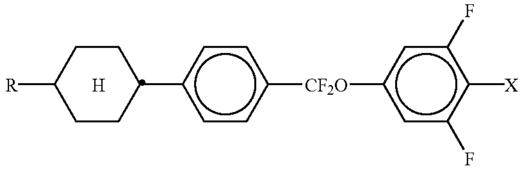
I34
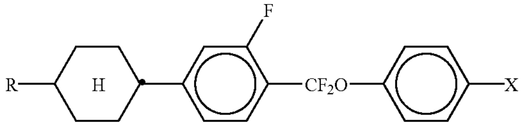
I35
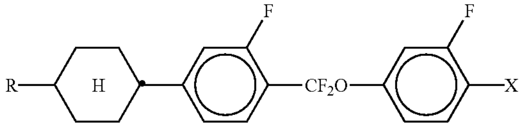
I36
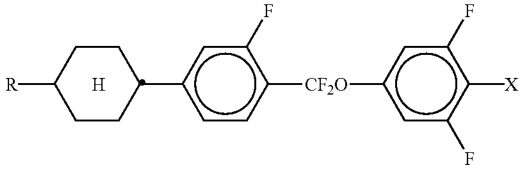
I37
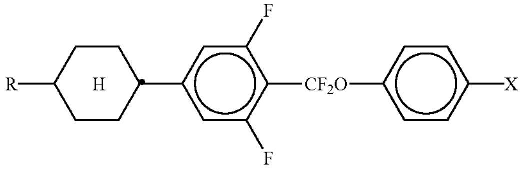
I38
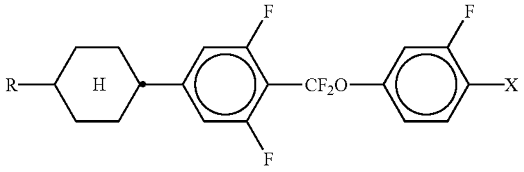
I39
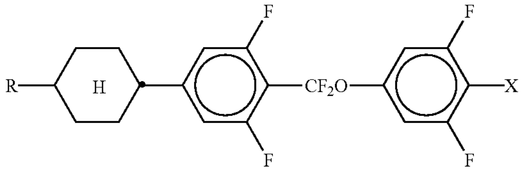
I40
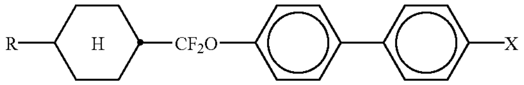
-continued
I41
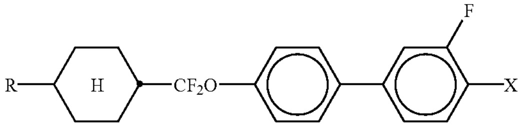
I42
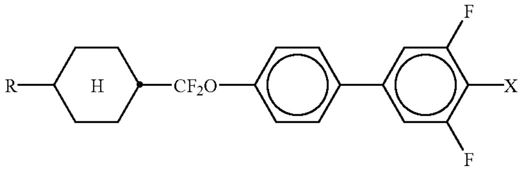
I43
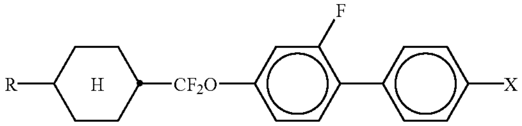
I44
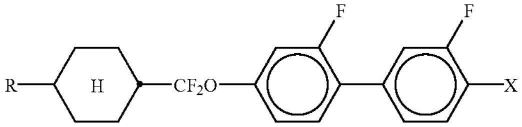
I45
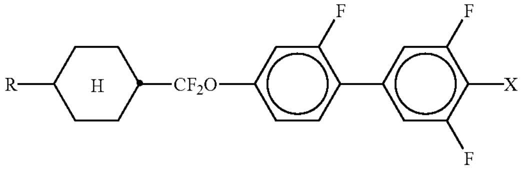
I46
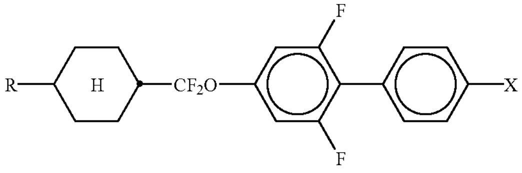
I47
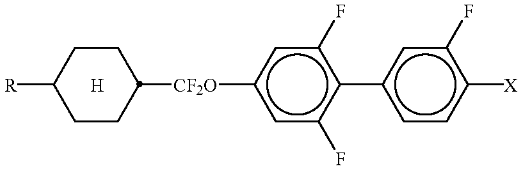
I48
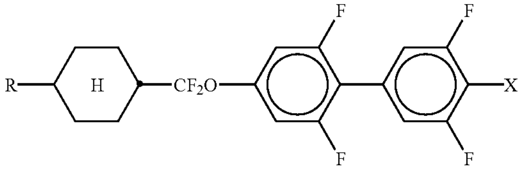
I49
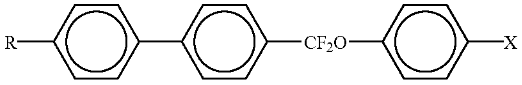

-continued
I50
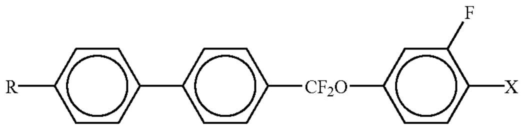
I51
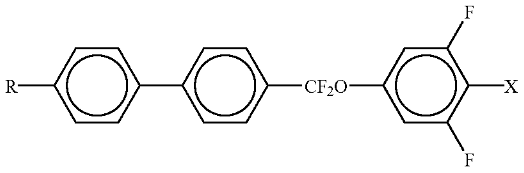
I52
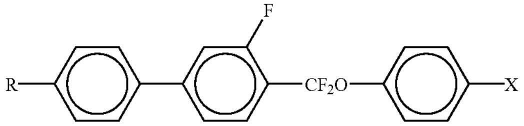
I53
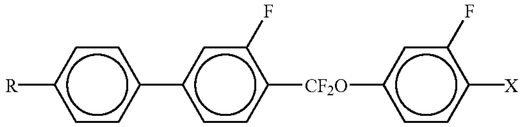
I54
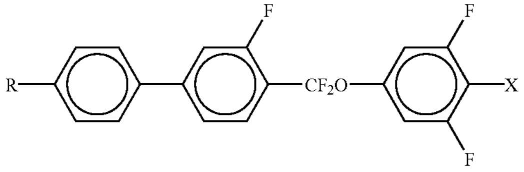
I55
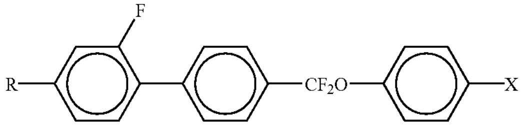
I56
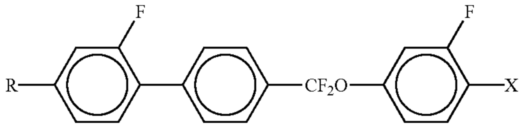
I57
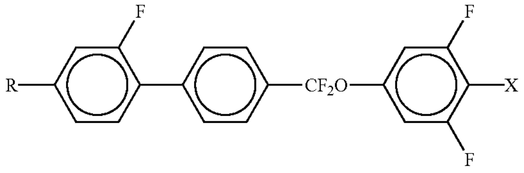
I58
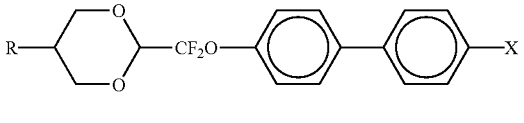
-continued
I59
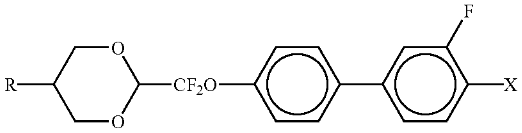
I60
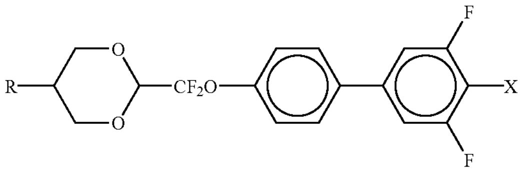
I61
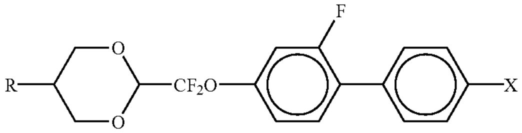
I62
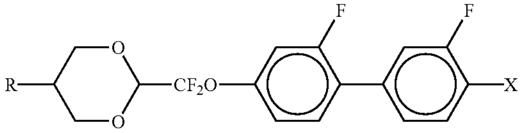
I63
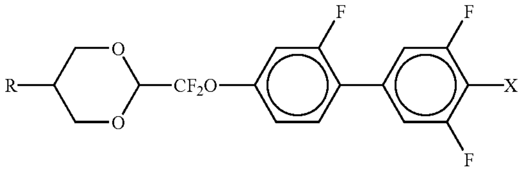
I64
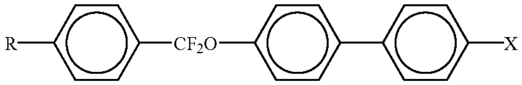
I65
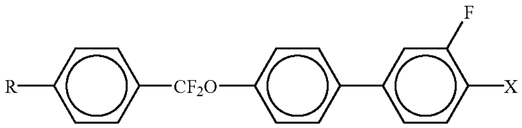
I66
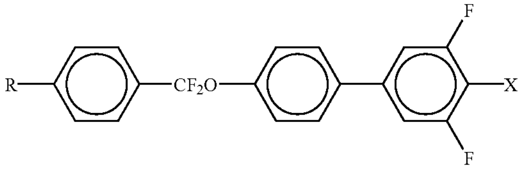
I67
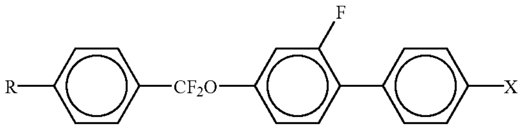

-continued
I68
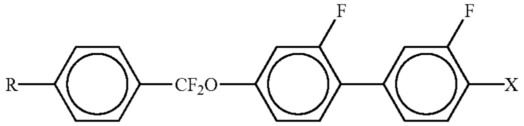
I69
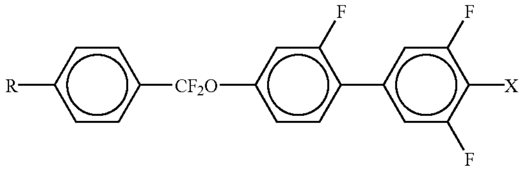
I70
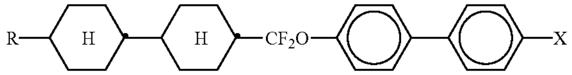
I71
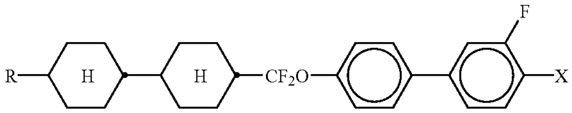
I72
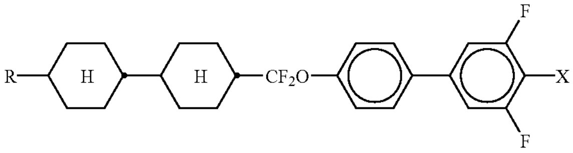
I73
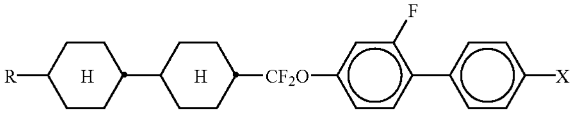
I74
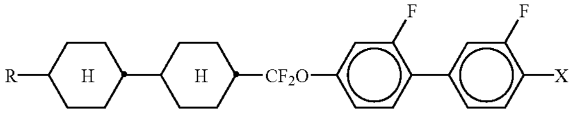
I75
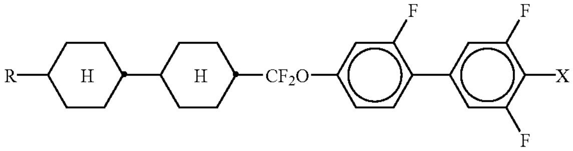
I76
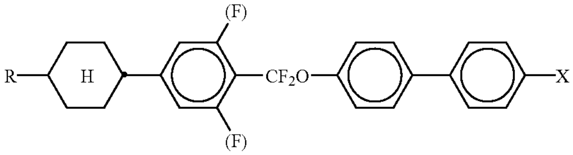
-continued
I77
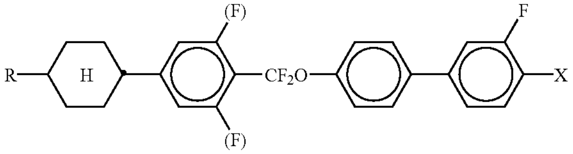
I78
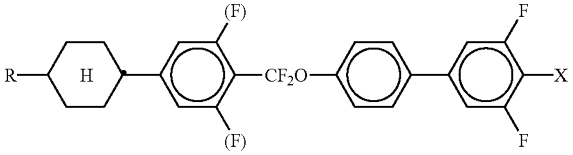
I79
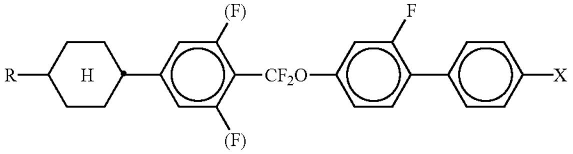
I80
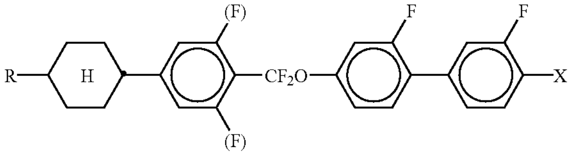
I81
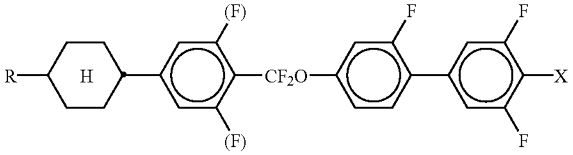
I82
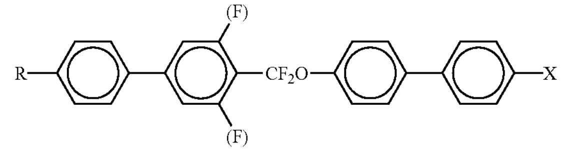
I83
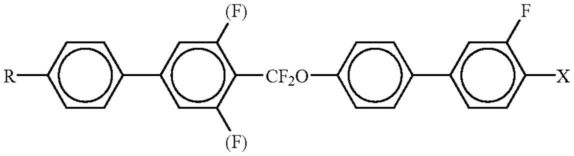
I84
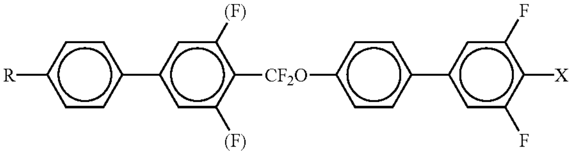

-continued
I85
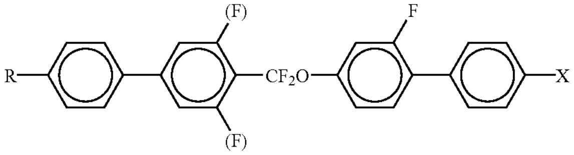
I86
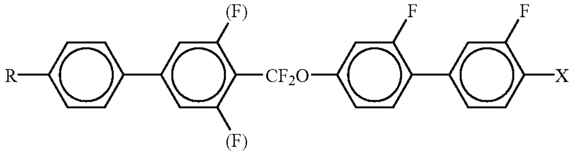
I87
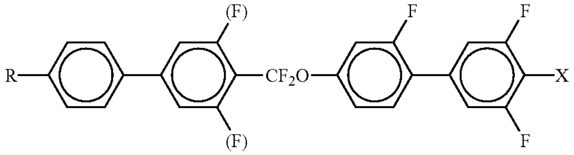
I88
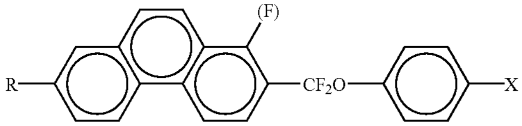
I89
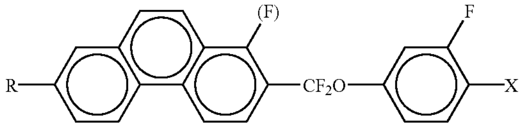
I90
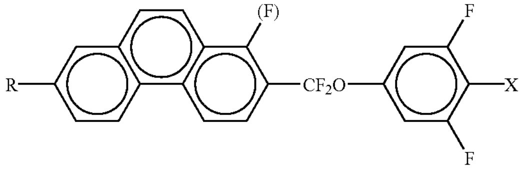
I91
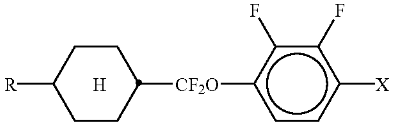
I92
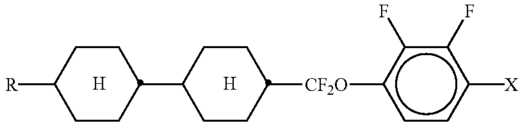
I93
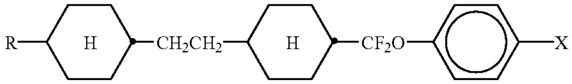
-continued
I94
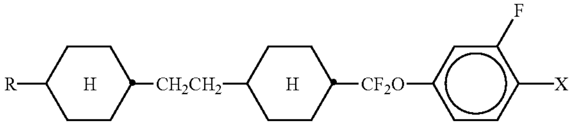
I95
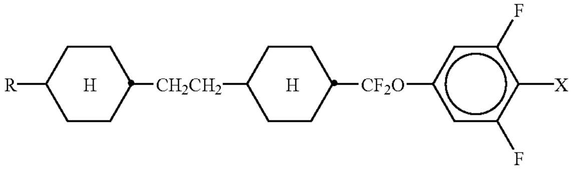
I96
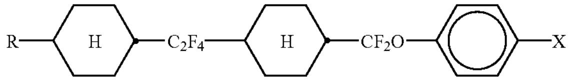
I97
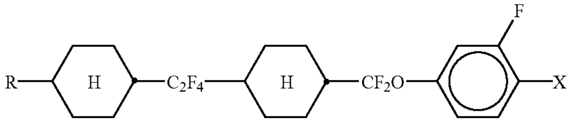
I98
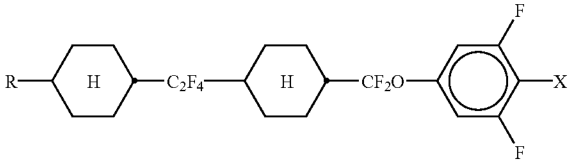
I99
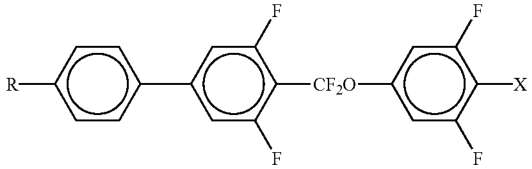
I100
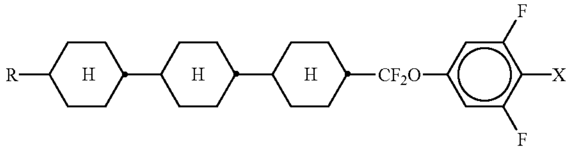
I101
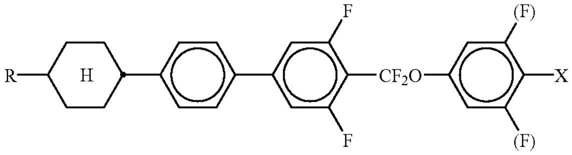
I102
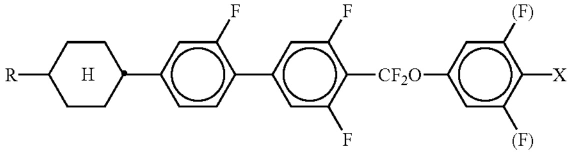

-continued

I103

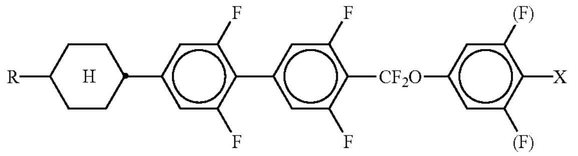

I104

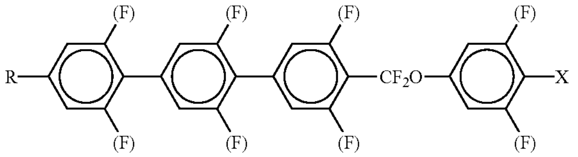

-continued

I105

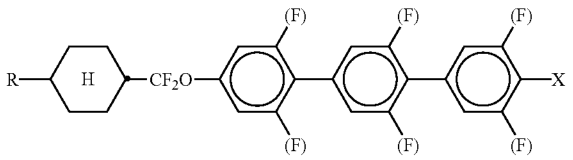

wherein (F) means fluorine or hydrogen.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

The compounds according to the invention can be prepared, for example, as follows:

Scheme 1

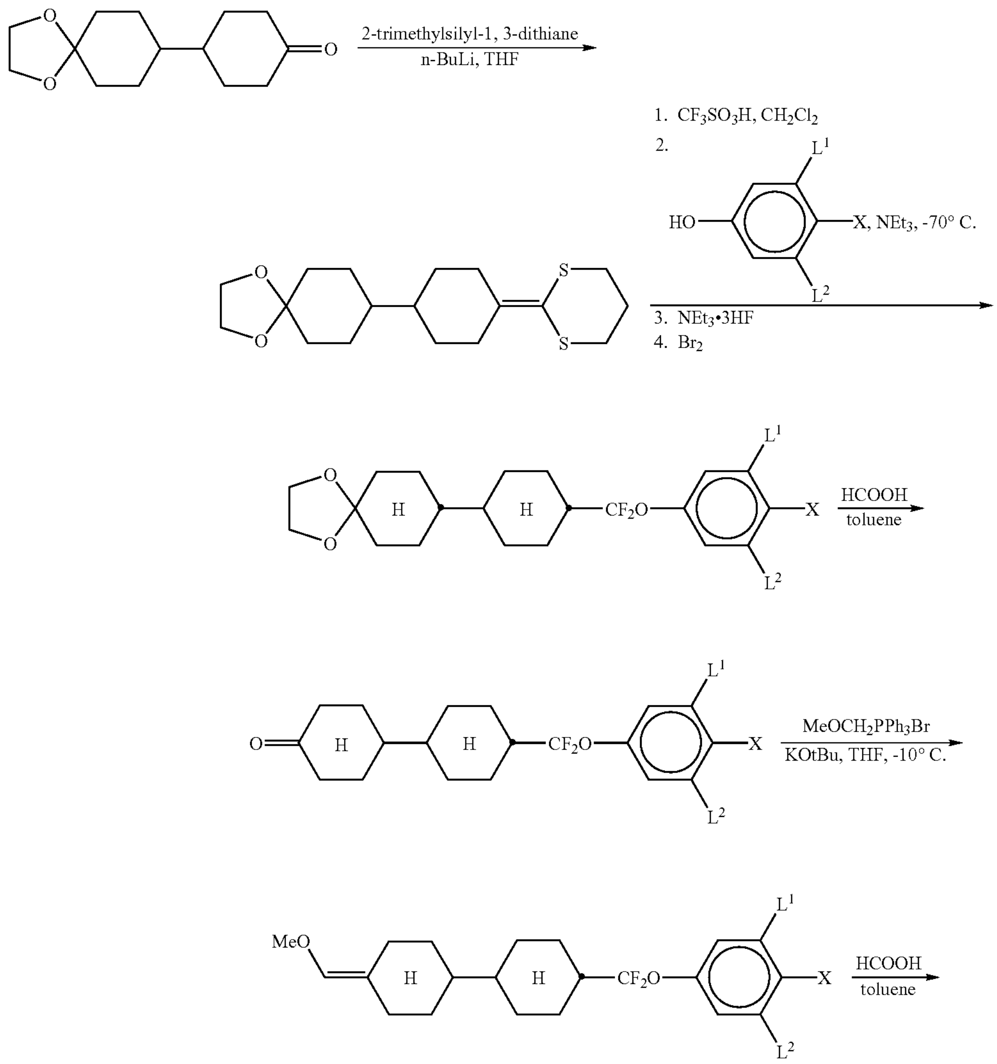

-continued
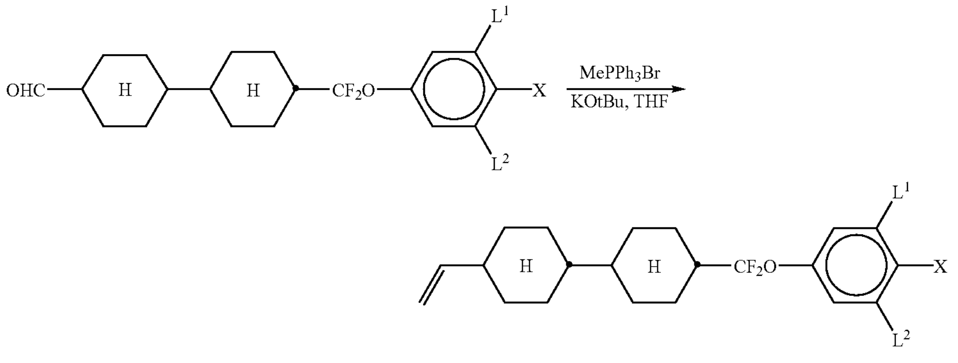
Scheme 2
(alkyl: straight-chain or branched alkyl radical having 1–9 carbon atoms)
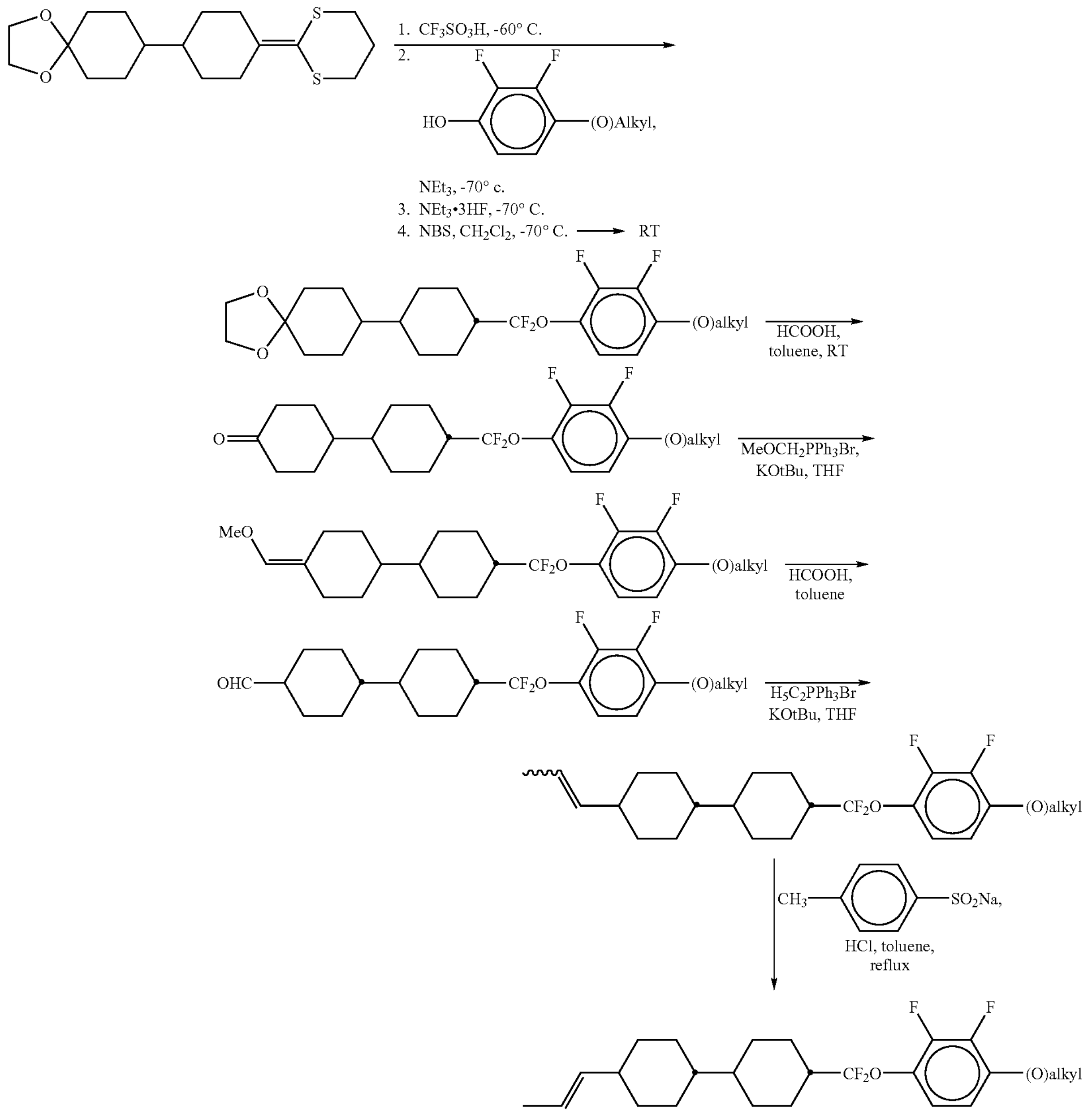

Scheme 3
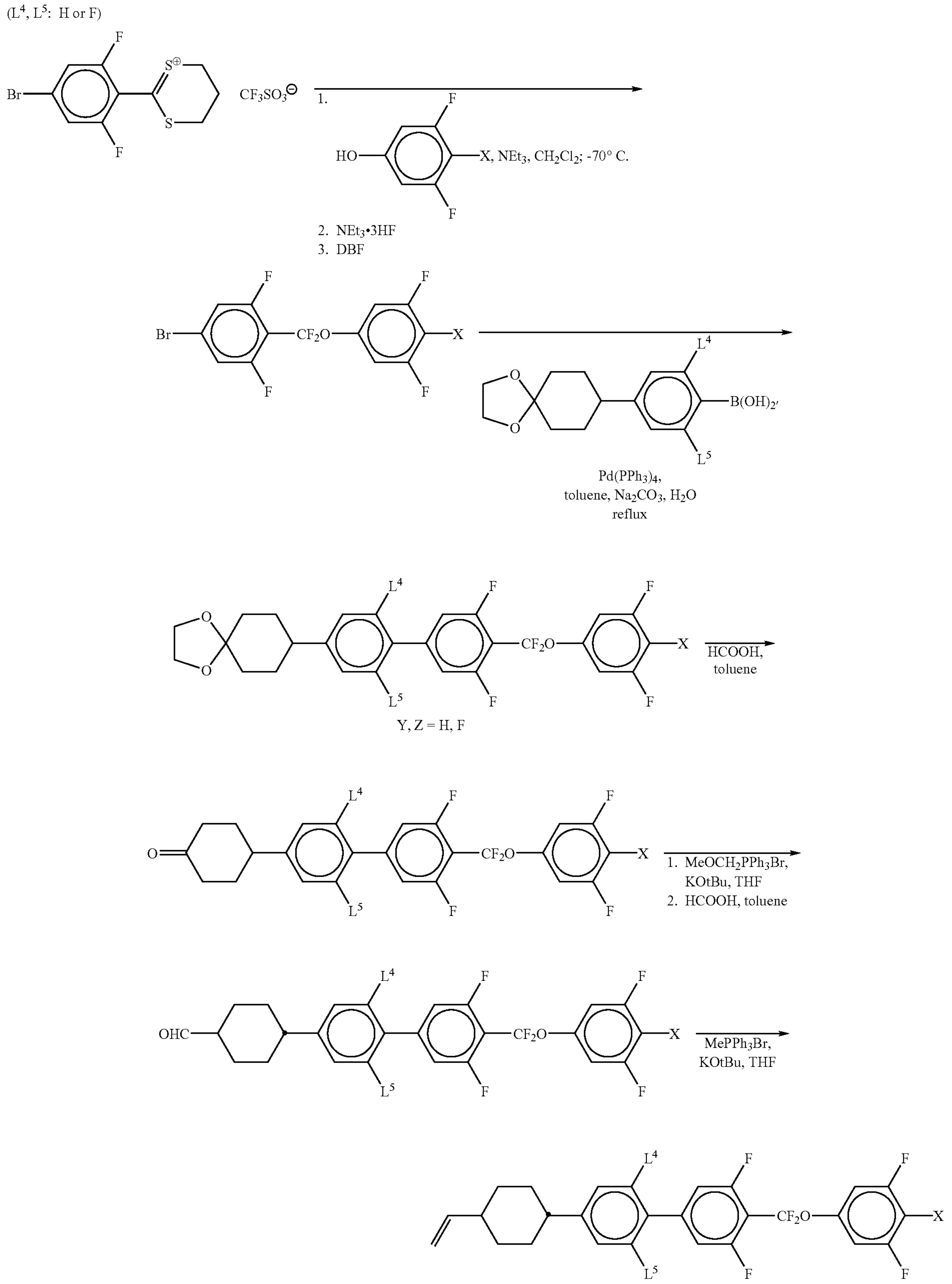

Scheme 4

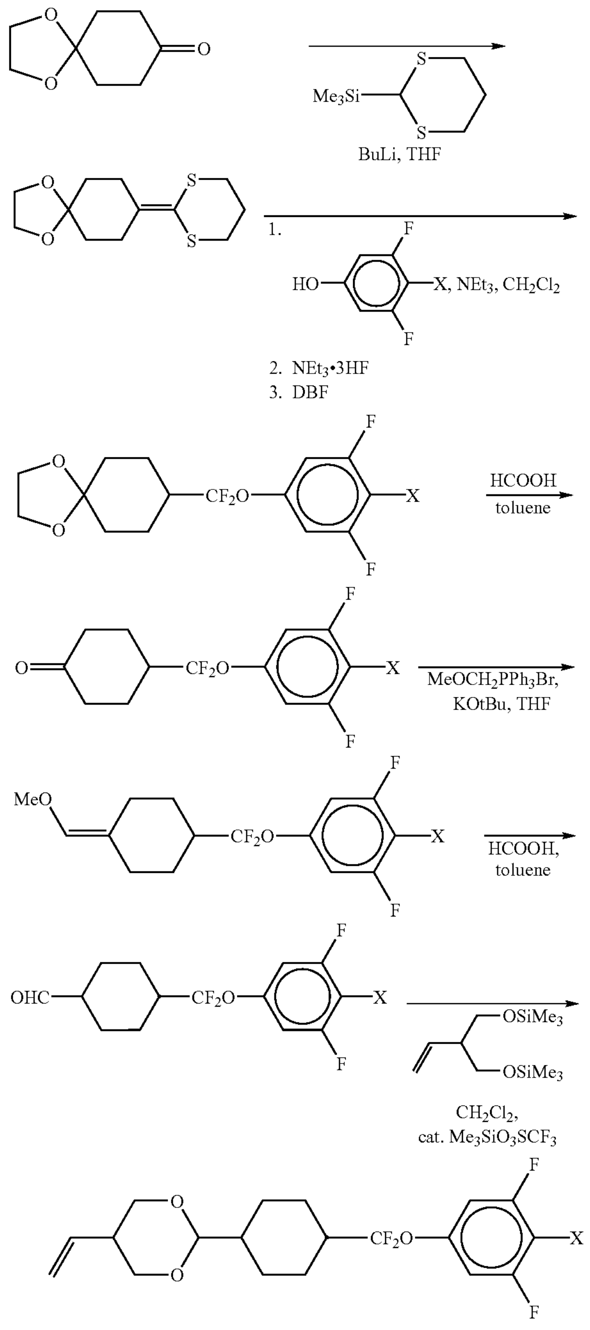

The invention also relates to electro-optical displays (in particular STN or MLC displays having two plane-parallel outer plates, which, together with a frame, form a cell, integrated non-linear elements for switching individual pixels on the outer plates, and a nematic liquid-crystal mixture of positive dielectric anisotropy and high specific resistance which is located in the cell) which contain media of this type, and to the use of these media for electro-optical purposes.

The liquid-crystal mixtures according to the invention enable a significant widening of the available parameter latitude.

The achievable combinations of clearing point, viscosity at low temperature, thermal and UV stability and dielectric anisotropy are far superior to previous materials from the prior art.

The requirement for a high clearing point, a nematic phase at low temperature and a high $\Delta\epsilon$ has hitherto only been achieved to an inadequate extent. Although liquid-crystal mixtures such as, for example, MLC-6476 and MLC-6625 (Merck KGaA, Darmstadt, Germany) have comparable clearing points and low-temperature stabilities, they have, however, relatively low $\Delta n$ values and also higher threshold voltages of about ≧1.7 V.

Other mixture systems have comparable viscosities and $\Delta\in$ values, but only have clearing points in the region of 60° C.

The liquid-crystal mixtures according to the invention, while retaining the nematic phase down to −20° C. and preferably down to −30° C., particularly preferably down to −40° C., enable clearing points above 80° C., preferably above 90° C., particularly preferably above 100° C., simultaneously dielectric anisotropy values $\Delta\epsilon$ of ≧4, preferably ≧6, and a high value for the specific resistance to be achieved, enabling excellent STN and MLC displays to be obtained. In particular, the mixtures are characterised by low operating voltages. The TN thresholds are below 1.5 V, preferably below 1.3 V.

It goes without saying that, through a suitable choice of the components of the mixtures according to the invention, it is also possible for higher clearing points (for example above 110°) to be achieved at a higher threshold voltage or lower clearing points to be achieved at lower threshold voltages with retention of the other advantageous properties. At viscosities correspondingly increased only slightly, it is likewise possible to obtain mixtures having greater $\Delta\epsilon$ and thus lower thresholds. The MLC displays according to the invention preferably operate at the first Gooch and Tarry transmission minimum [C. H. Gooch and H. A. Tarry, Electron. Lett. 10, 2-4, 1974; C. H. Gooch and H. A. Tarry, Appl. Phys., Vol. 8,1575-1584, 1975] are used, where, besides particularly favorable electro-optical properties, such as, for example, high steepness of the characteristic line and low angle dependence of the contrast (German Patent 30 22 818), a lower dielectric anisotropy is sufficient at the same threshold voltage as in an analogous display at the second minimum. This enables significantly higher specific resistances to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

The flow viscosity $v_{20}$ at 20° C. is preferably <60 $mm^2 \cdot s^{-1}$, particularly preferably <50 $mm^2 \cdot s^{-1}$. The nematic phase range is preferably at least 90°, in particular at least 100°. This range preferably extends at least from −30° to +80°.

Measurements of the capacity holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I exhibit a significantly smaller decrease in the HR with increasing temperature than, for example, analogous mixtures comprising cyanophenylcyclohexanes of the formula

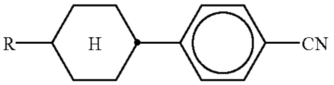

or esters of the formula

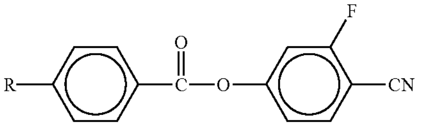

instead of the compounds of the formula I.

The UV stability of the mixtures according to the invention is also considerably better, i.e. they exhibit a significantly smaller decrease in the HR on exposure to UV.

The media according to the invention are preferably based on a plurality of (preferably two, three or more) compounds of the formula I, i.e. the proportion of these compounds is 5-95%, preferably 10-60% and particularly preferably in the range 15-40%.

The individual compounds of the formulae I to IX and their sub-formulae which can be used in the media according to the invention are either known or they can be prepared analogously to the known compounds.

Preferred embodiments are indicated below:

The medium preferably comprises one, two or three homologous compounds of the formula I, where each homologue is present in the mixture in a maximum proportion of 10%.

Medium additionally comprises one or more compounds selected from the group consisting of the general formulae II to IX:

II

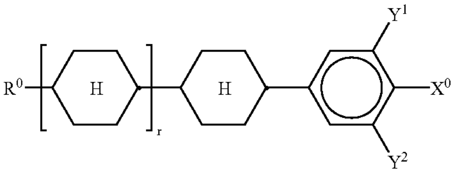

III

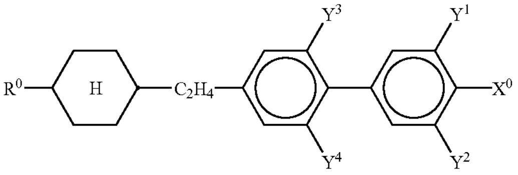

IV

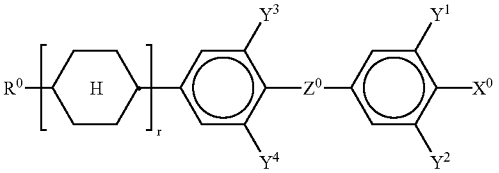

-continued

V

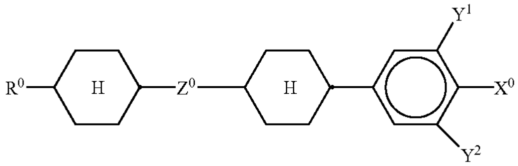

VI

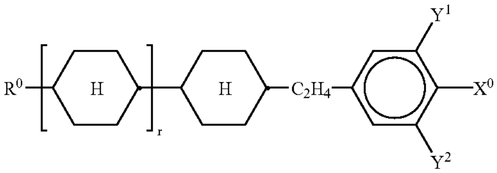

VII

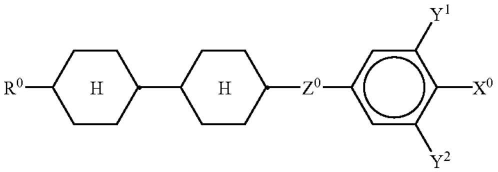

VIII

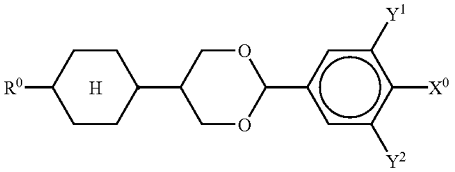

IX

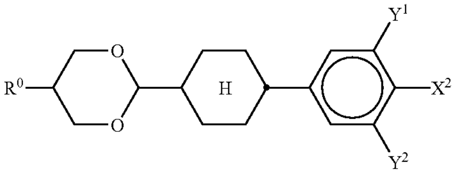

in which the individual radicals have the following meanings:

$R^0$ is n-alkyl, oxaalkyl, fluoroalkyl, alkenyloxy or alkenyl, each having up to 9 carbon atoms, $X^0$ is F, Cl, halogenated alkyl, halogenated alkenyl, halogenated alkenyloxy or halogenated alkoxy having up to 7 carbon atoms, $Z^0$ is $—CH═CH—$, $—C_2H_4—$, $—(CH_2)_4—$, $—C_2F_4—$, $—CF═CF—$, $—CF_2O—$, $—OCF_2—$ or $—COO—$, $Y^1$, $Y^2$, $Y^3$ and $Y^4$ are each, independently of one another, H or F, and r is 0 or 1.

The compound of the formula IV is preferably

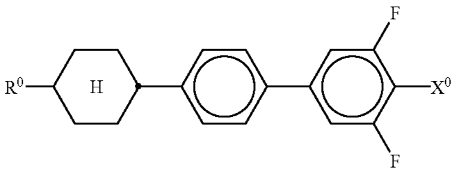

-continued
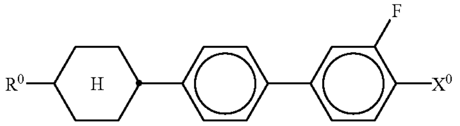
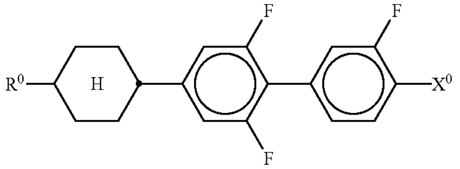
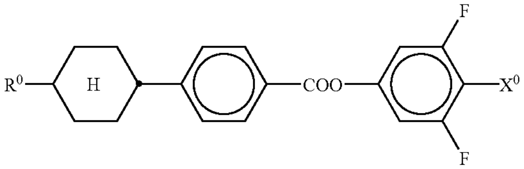
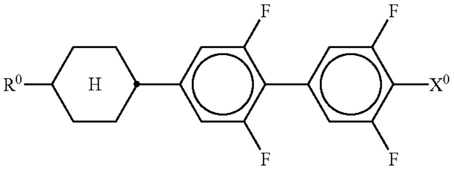
or
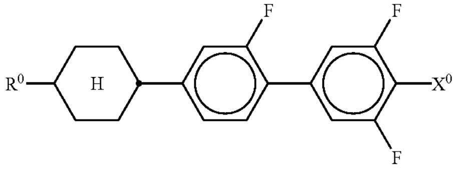
The medium additionally comprises one or more compounds of the formulae
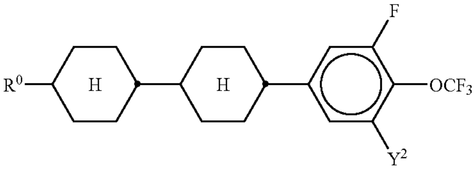
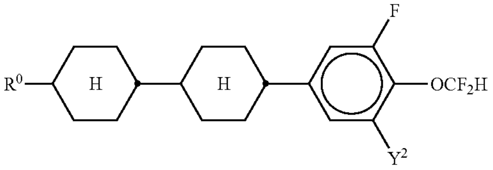
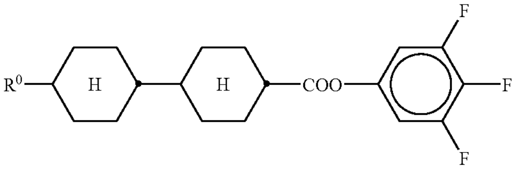
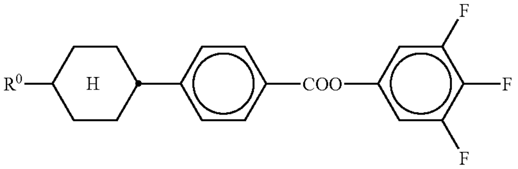
-continued
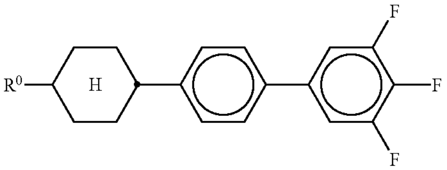
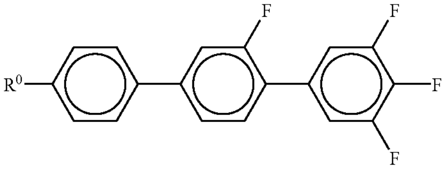
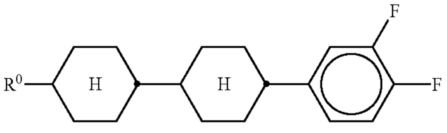
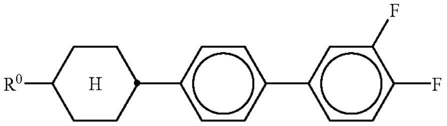
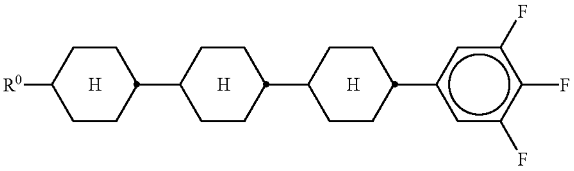
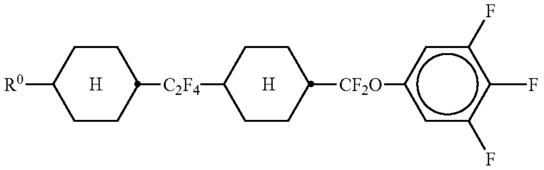
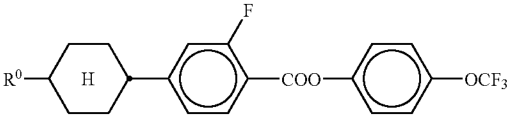
and/or
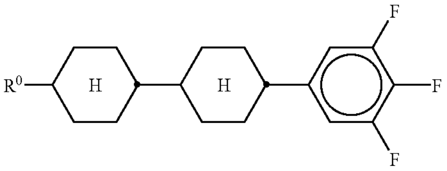
in which $R^0$ and $Y^2$ are as defined above.
The medium preferably comprises one, two or three, furthermore four, homologues of the compounds selected from the group consisting of H1 to H18 (n=1-7):
H1
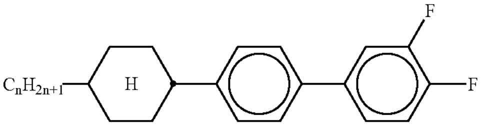

-continued
H2
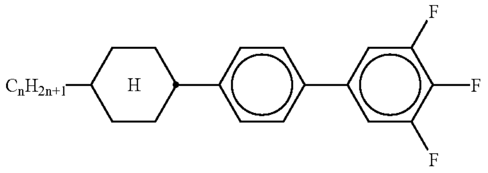
H3
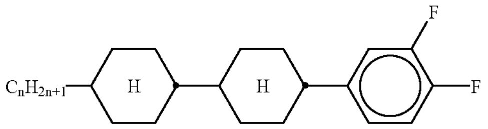
H4
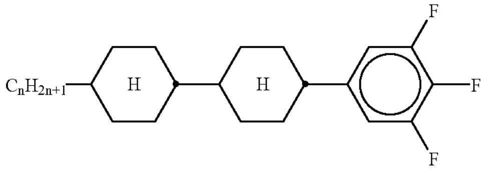
H5
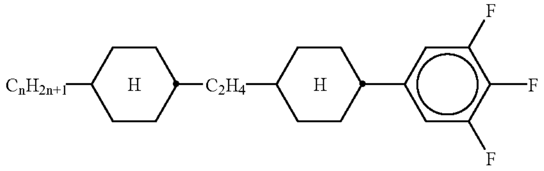
H6
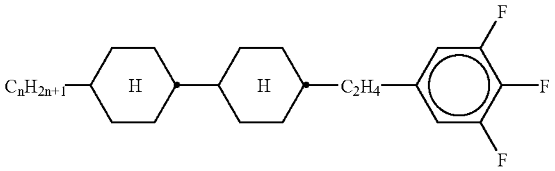
H7
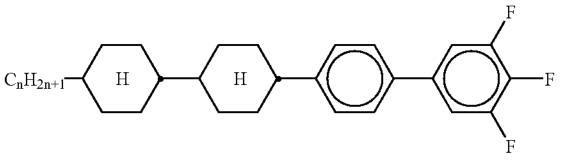
H8
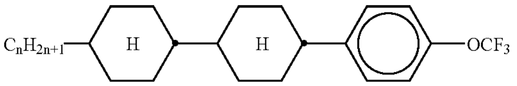
H9
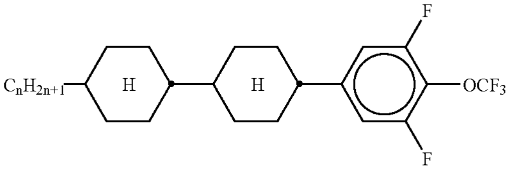
H10
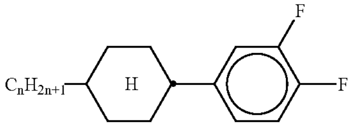
-continued
H11
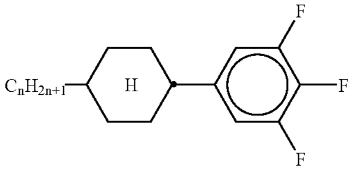
H12
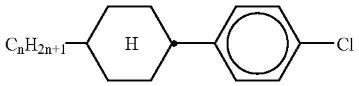
H13
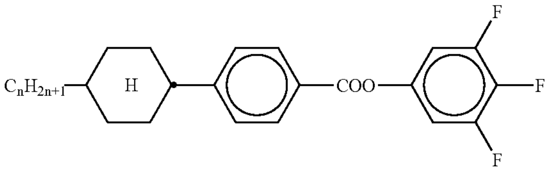
H14
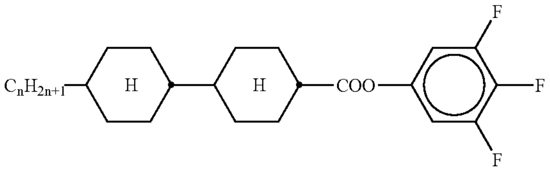
H15
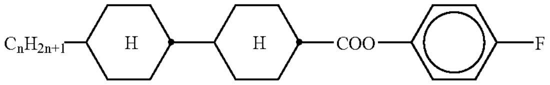
H16
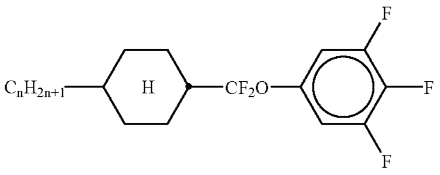
H17
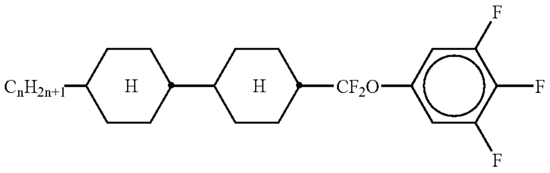
H18
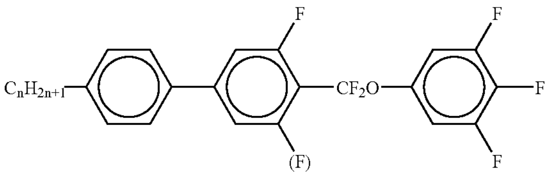

The medium additionally comprises one or more compounds selected from the group consisting of the general formulae X to XV:

X

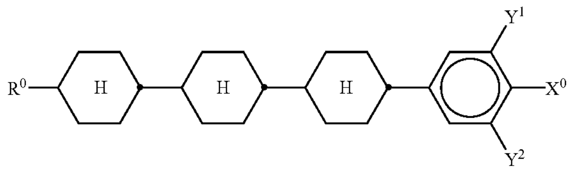

XI

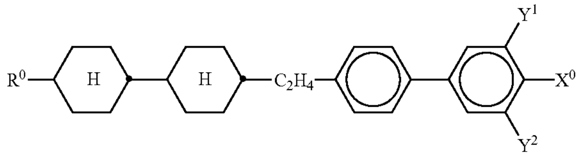

XII

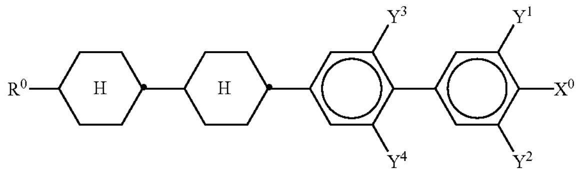

XIII

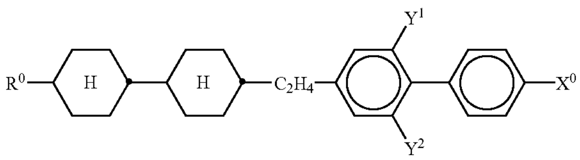

XIV

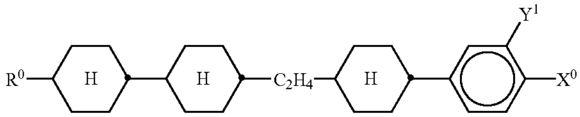

XV

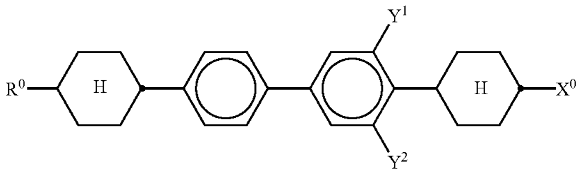

in which $R^0$, $X^0$, $Y^1$, $Y^2$, $Y^3$ and $Y^4$ are each, independently of one another, as defined in claim 7. $X^0$ is preferably F, Cl, $CF_3$, $OCF_3$ or $OCHF_2$. $R^0$ is preferably alkyl, oxaalkyl, fluoroalkyl, alkenyl or alkenyloxy.

The proportion of compounds of the formulae I to IX together in the mixture as a whole is at least 50% by weight.

The proportion of compounds of the formula I in the mixture as a whole is from 5 to 50% by weight.

The proportion of compounds of the formulae II to IX in the mixture as a whole is from 30 to 70% by weight.

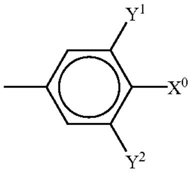 is preferably

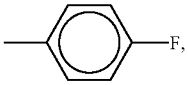, 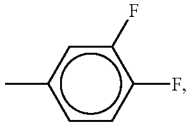,

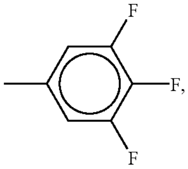, 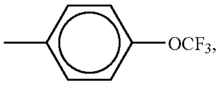,

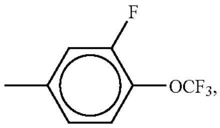, 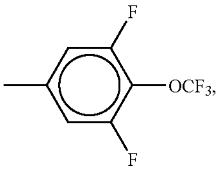,

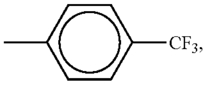, 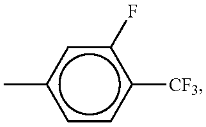,

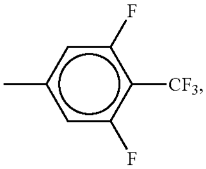, 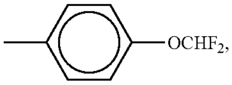,

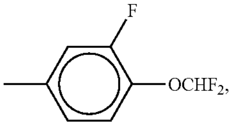, 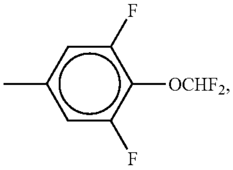,

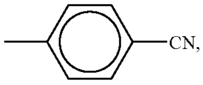, 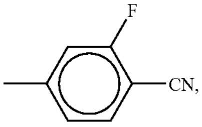,

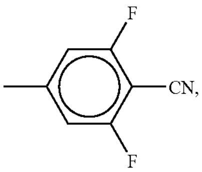, 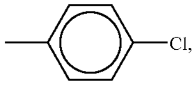,

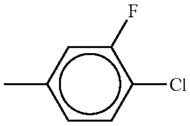 or 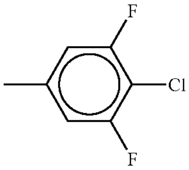

The medium comprises compounds of the formulae II, III, IV, V, VI, VII, VII and/or IX.

$R^0$ is straight-chain alkyl or alkenyl having from 2 to 7 carbon atoms.

The medium essentially consists of compounds of the formulae I to XV.

The medium comprises further compounds, preferably selected from the following group consisting of the general formulae XVI to XX:

XVI

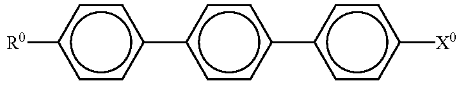

XVII

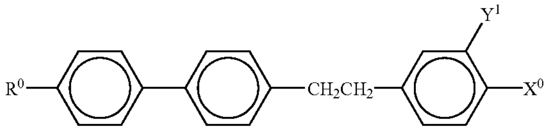

XVIII

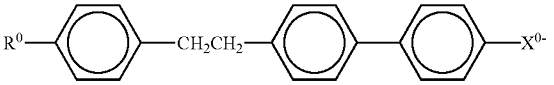

XIX

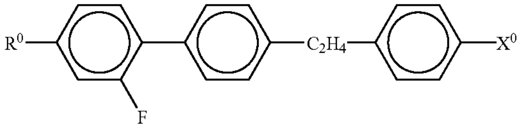

XX

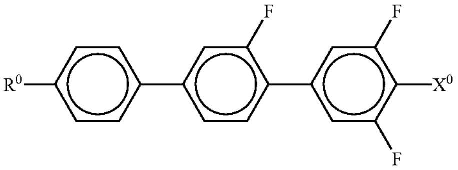

in which $R^0$ and $X^0$ are as defined above, and the 1,4-phenylene rings may be substituted by CN, chlorine or fluorine. The 1,4-phenylene rings are preferably monosubstituted or polysubstituted by fluorine atoms.

The medium comprises further compounds, preferably selected from the following group consisting of the formulae RI to RXI

RI

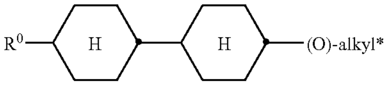

RII

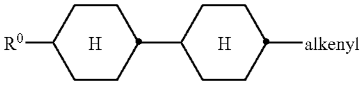

RIII

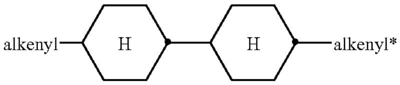

RIV

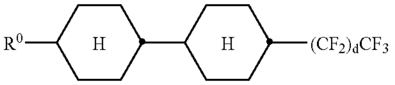

-continued

RV

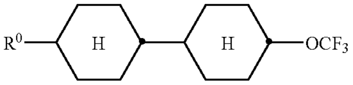

RVI

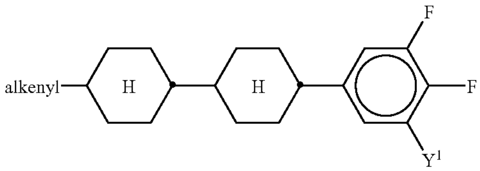

RVII

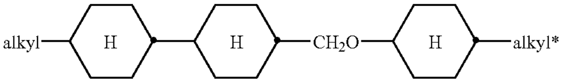

RVIII

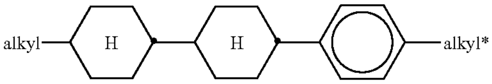

RIX

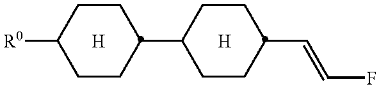

RX

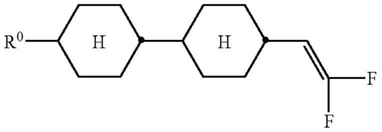

RXI

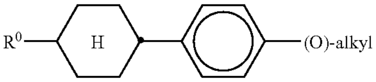

in which $R^0$ is n-alkyl, oxaalkyl, fluoroalkyl, alkenyloxy or alkenyl, each having up to 9 carbon atoms, d is 0, 1 or 2, $Y^1$ is H or F, alkyl and alkyl* are each, independently of one another, a straight-chain or branched alkyl radical having 1-9 carbon atoms, alkenyl and alkenyl* are each, independently of one another, a straight-chain or branched alkenyl radical having up to 9 carbon atoms.

The medium preferably comprises one or more compounds of the formulae

RIa

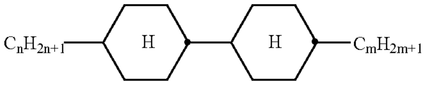

RIb

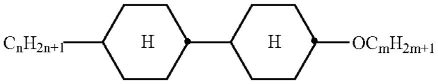

RIIa

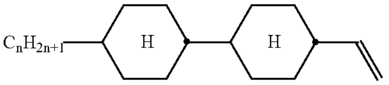

-continued

RIIb

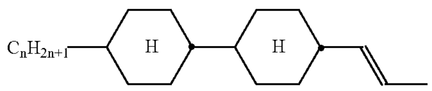

RIIIa

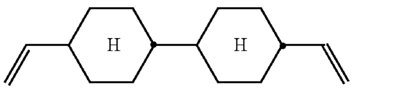

RIIIb

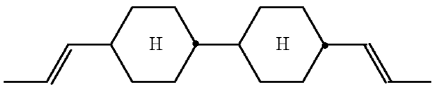

RIIIc

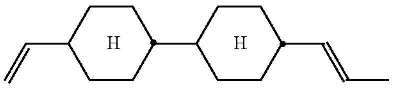

RIVa

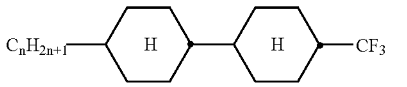

in which n and m are each an integer from 1-9.

The I:(II+III+IV+V+VI+VII+VII+IX) weight ratio is preferably from 1:10 to 10:1.

The medium essentially consists of compounds selected from the group consisting of the general formulae I to XV.

It has been found that even a relatively small proportion of compounds of the formula I mixed with conventional liquid-crystal materials, but in particular with one or more compounds of the formulae II, III, IV, V, VI, VII, VIII and/or IX, results in a significant lowering of the threshold voltage and in low birefringence values, with broad nematic phases with low smectic-nematic transition temperatures being observed at the same time, improving the shelf life. The compounds of the formulae I to IX are colorless, stable and readily miscible with one another and with other liquid-crystalline materials.

The term "alkyl" or "alkyl*" covers straight-chain and branched alkyl groups having 1-9 carbon atoms, in particular the straight-chain groups methyl, ethyl, propyl, butyl, pentyl, hexyl and heptyl. Groups having 2-5 carbon atoms are generally preferred.

The term "alkenyl" or "alkenyl*" covers straight-chain and branched alkenyl groups having up to 9 carbon atoms, in particular the straight-chain groups. Preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably=1 and m is preferably from 1 to 6.

Through a suitable choice of the meanings of $R^0$ and $X^0$, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio of the elastic constants $k_{33}$ (bend) and $k_{11}$ (splay) compared with alkyl or alkoxy radicals. 4-alkenyl radicals, 3-alkenyl radicals and the like generally give lower threshold voltages and smaller values of $k_{33}/k_{11}$ compared with alkyl and alkoxy radicals.

A —$CH_2CH_2$— group in $Z^1$ and/or $Z^2$ generally results in higher values of $k_{33}/k_{11}$ compared with a single covalent bond. Higher values of $k_{33}/k_{11}$ facilitate, for example, flatter transmission characteristic lines in TN cells with a 90° twist (in order to achieve grey shades) and steeper transmission characteristic lines in STN, SBE and OMI cells (greater multiplexability), and vice versa.

The optimum mixing ratio of the compounds of the formulae I and II+III+IV+V+VI+VII+VIII+IX depends substantially on the desired properties, on the choice of the components of the formulae I, II, III, IV, V, VI, VII, VIII and/or IX, and the choice of any other components that may be present. Suitable mixing ratios within the range given above can easily be determined from case to case.

The total amount of compounds of the formulae I to XV in the mixtures according to the invention is not crucial. The mixtures can therefore comprise one or more further components for the purposes of optimising various properties. However, the observed effect on the addressing times and the threshold voltage is generally greater, the higher the total concentration of compounds of the formulae I to XV.

In a particularly preferred embodiment, the media according to the invention comprise compounds of the formulae II to IX (preferably II and/or III) in which $X^0$ is $OCF_3$, $OCHF_2$, F, $OCH{=}CF_2$, $OCF{=}CF_2$, $OCF_2CHFCF_3$ or $OCF_2$—$CF_2H$. A favorable synergistic effect with the compounds of the formula I results in particularly advantageous properties.

The construction of the MLC display according to the invention from polarizers, electrode base plates and surface-treated electrodes corresponds to the conventional construction for displays of this type. The term "conventional construction" is broadly drawn here and also covers all derivatives and modifications of the MLC display, in particular including matrix display elements based on poly-Si TFT or MIM.

A significant difference between the displays according to the invention and the conventional displays based on the twisted nematic cell consists, however, in the choice of the liquid-crystal parameters of the liquid-crystal layer.

The liquid-crystal mixtures which can be used in accordance with the invention are prepared in a manner conventional per se. In general, the desired amount of the components used in the lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature, such as, for example, stabilisers and antioxidants. For example, 0-15% of pleochroic dyes or chiral dopants can be added.

C denotes a crystalline phase, S a smectic phase, $S_C$ a smectic C phase, $S_B$ a smectic B phase, N a nematic phase and I the isotropic phase.

$V_{10}$ denotes the voltage for 10% transmission (viewing angle perpendicular to the plate surface). $t_{on}$ denotes the switch-on time and $t_{off}$ the switch-off time at an operating voltage corresponding to 2 times the value of $V_{10}$. $\Delta n$ denotes the optical anisotropy and $n_0$ the refractive index. $\Delta\epsilon$ denotes the dielectric anisotropy ($\Delta\epsilon=\epsilon_{\parallel}-\epsilon_{\perp}$, where $\epsilon_{\parallel}$ denotes the dielectric constant parallel to the longitudinal molecular axes and $\epsilon_{\perp}$ denotes the dielectric constant perpendicular thereto). The electro-optical data were measured in a TN cell at the 1 st minimum (i.e. at a $d\cdot\Delta n$ value of 0.5) at 20° C., unless expressly stated otherwise. The optical data were measured at 20° C., unless expressly stated otherwise.

The entire disclosures of all applications, patents and publications, cited herein and of corresponding German application No. 10148356.2, filed Sep. 29, 2001 are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively; n and m are in each case, independently of one another, 1, 2, 3, 4, 5, 6, 7, 8, 9, 10, 11, 12, 13, 14 or 15. The coding in Table B is self-evident. In Table A, only the acronym for the parent structure is indicated. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| $nCF_3$ | $C_nH_{2n+1}$ | $CF_3$ | H | H |
| $nOCF_3$ | $C_nH_{2n+1}$ | $OCF_3$ | H | H |
| $nOCF_2$ | $C_nH_{2n+1}$ | $OCHF_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nAm | $C_nH_{2n+1}$ | $COOC_mH_{2m+1}$ | H | H |
| $nOCCF_2$.F.F | $C_nH_{2n+1}$ | $OCH_2CF_2H$ | F | F |

Preferred mixture components are shown in Tables A and B.

TABLE A

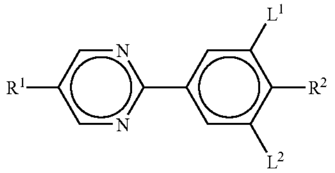

PYP

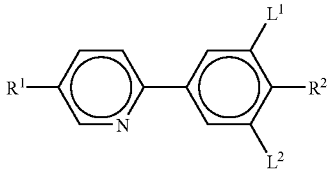

PYRP

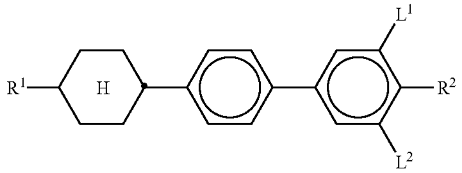

BCH

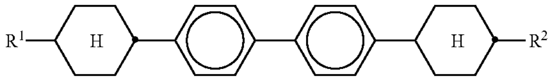

CBC

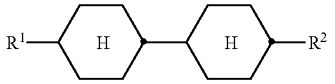

CCH

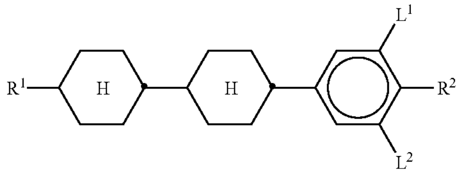

CCP

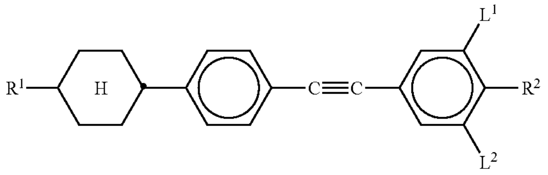

CPTP

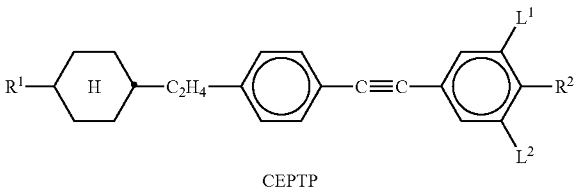

CEPTP

TABLE A-continued
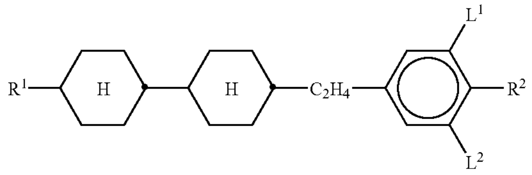
ECCP
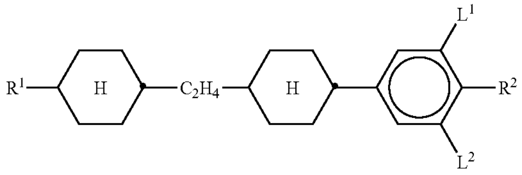
CECP
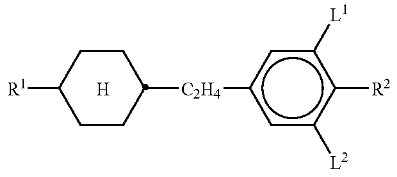
EPCH
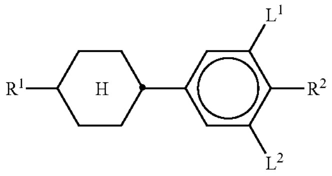
PCH
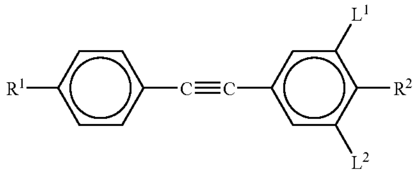
PTP
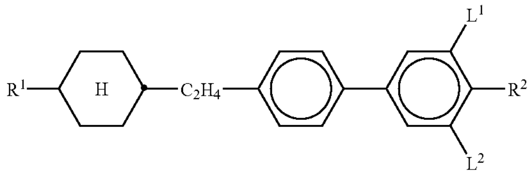
BECH
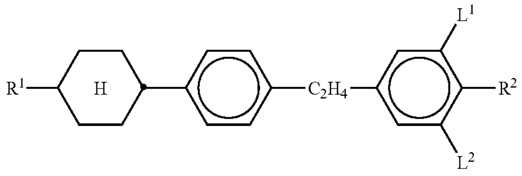
EBCH
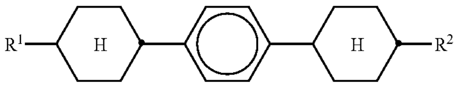
CPC
TABLE A-continued
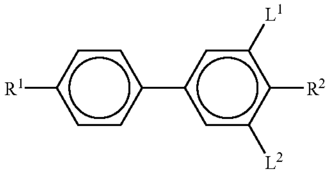
B
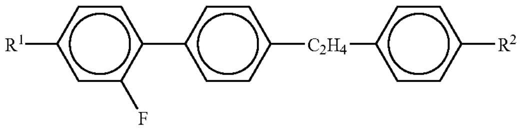
FET-nF
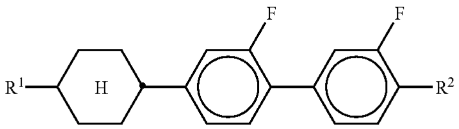
CGG
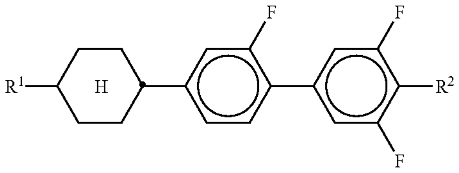
CGU
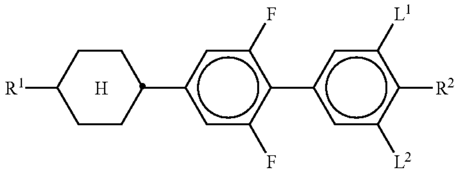
CUP
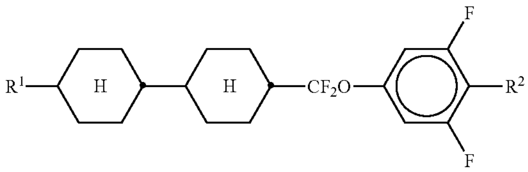
CCQU
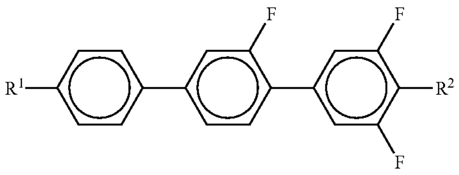
PGU TABLE B
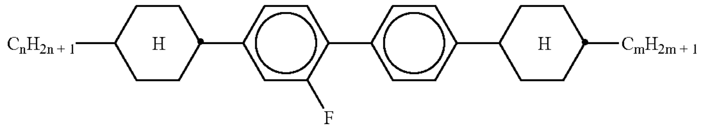
CBC-nmF
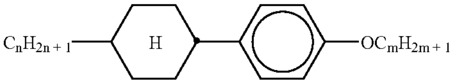
PCH-nOm
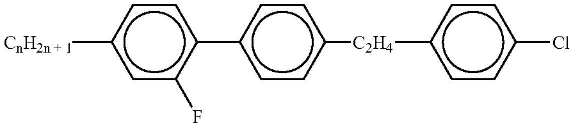
FET-nCl
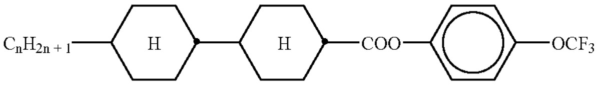
CP-nOCF$_3$
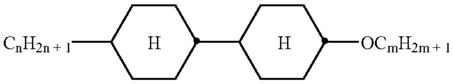
CCH-nOm
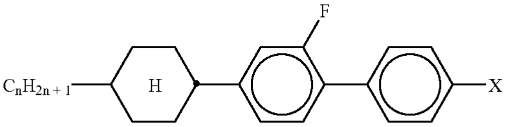
BCH-n.FX
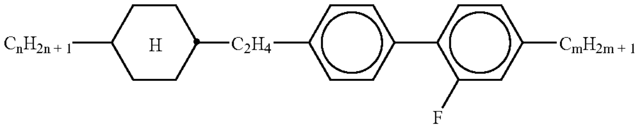
Inm
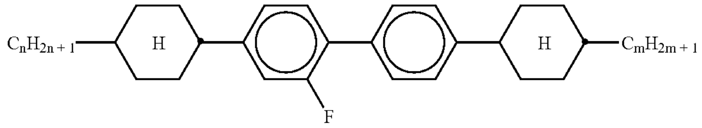
CBC-nmF
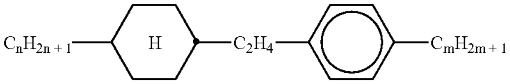
ECCP-nm
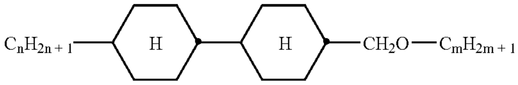
CCH-n1EM
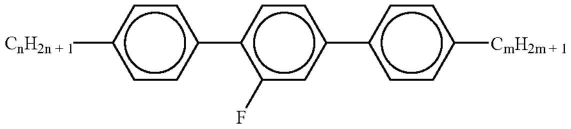
T-nFm
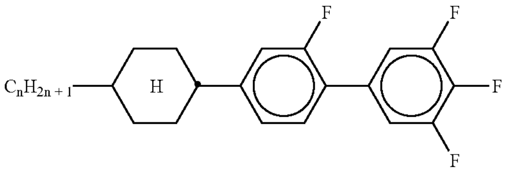
CGU-n-F
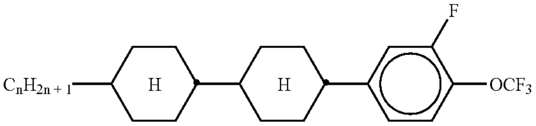
CCP-nOCF$_3$.F
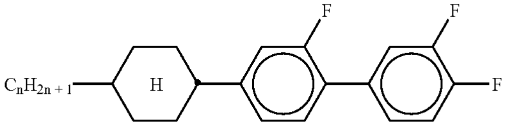
CGG-n-F
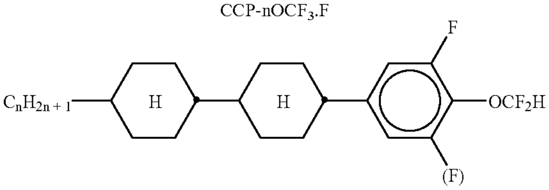
CCP-nOCF$_2$.F(.F)
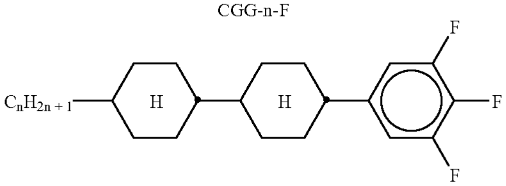
CCP-nF.F.F TABLE B-continued
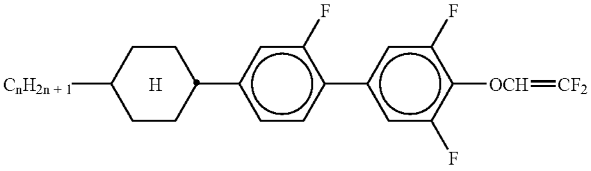
CGU-n-OXF
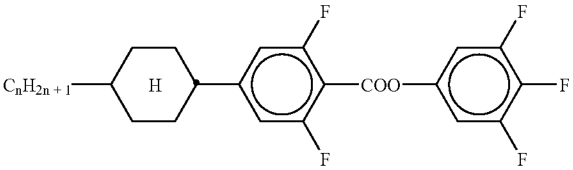
CUZU-n-F
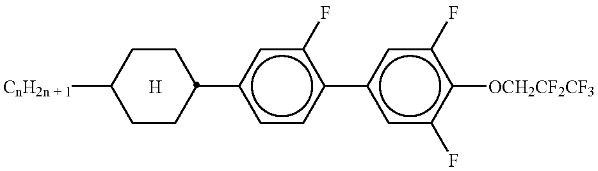
CGU-n-O1DT
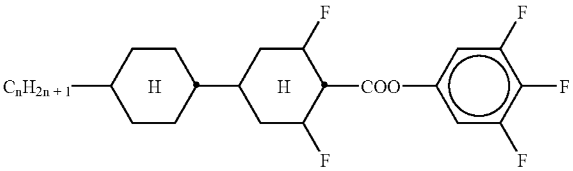
CGU-n-O1DT
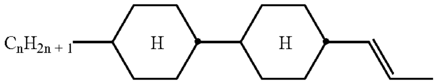
CC-n-V1
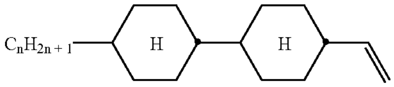
CC-n-V
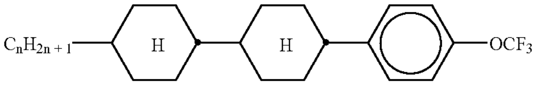
CCP-nOCF$_3$
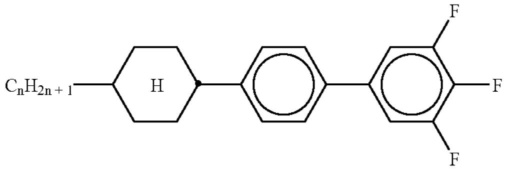
BCH-nF.F.F
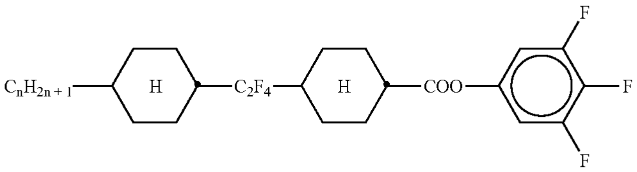
CWCZU-n-F
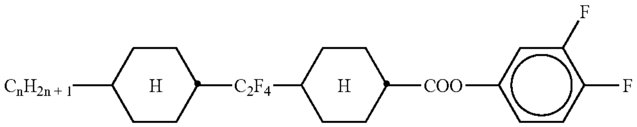
CWCZG-n-F
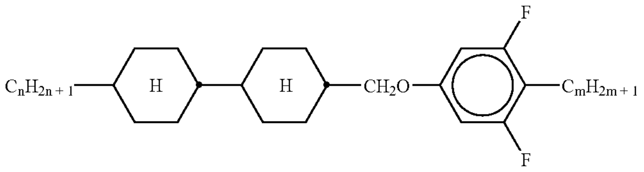
CCOC-n-m TABLE B-continued
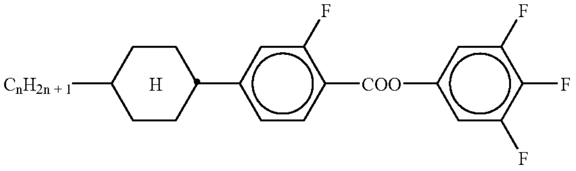
CGZU-n-F
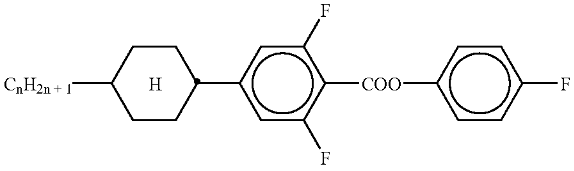
CUZP-n-F
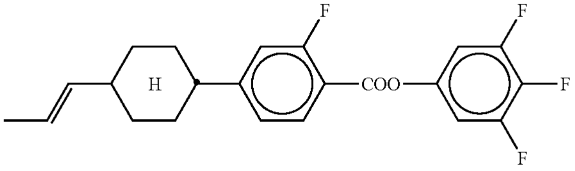
CGU-1V-F
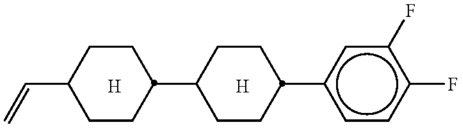
CCG-V-F
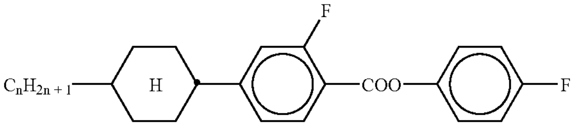
CGZP-n-F
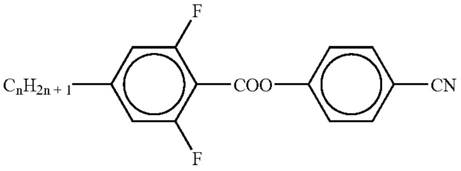
UZP-n-N
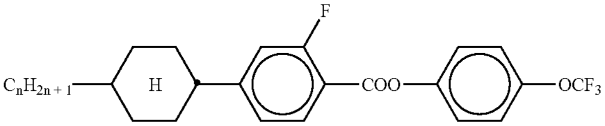
CGZP-n-OT
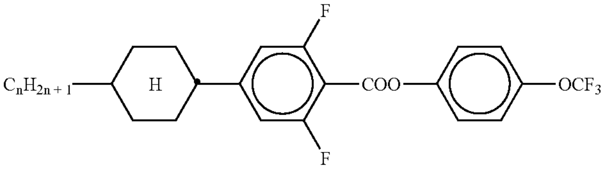
CUZP-n-OT
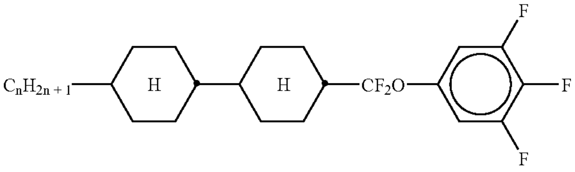
CCQU-n-F
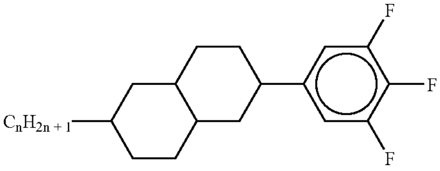
Dec-U-n-F
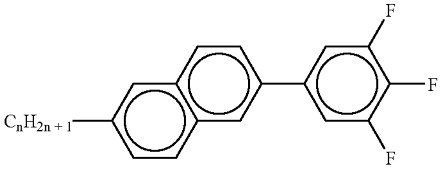
Nap-U-n-F
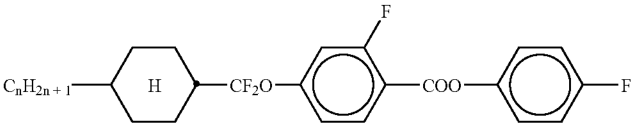
CQGZP-n-F TABLE B-continued
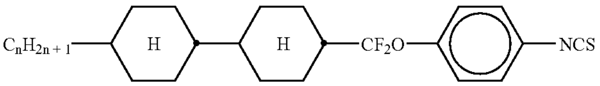
CCQP-n-S
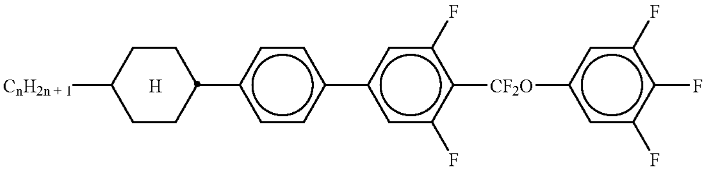
CPUQU-n-F
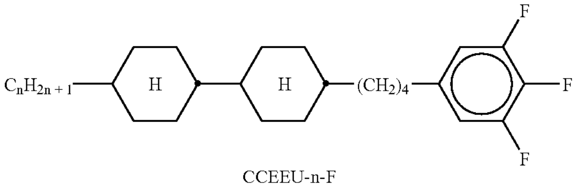
CCEEU-n-F
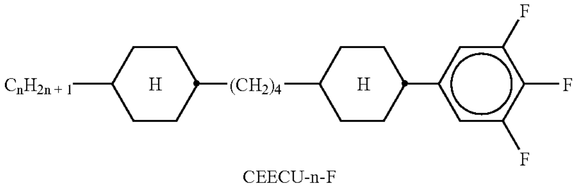
CEECU-n-F
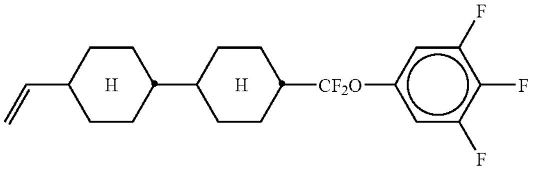
CCQU-V-F
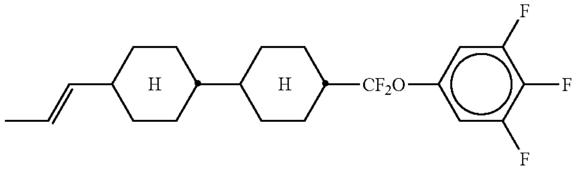
CCQU-1V-F
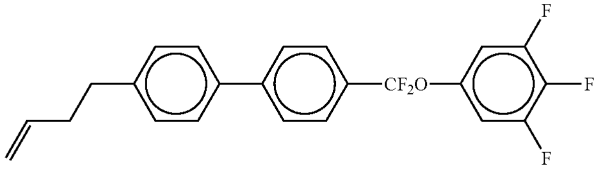
PUQU-V2-F
TABLE C
Table C shows possible dopants which are generally added to the mixtures according to the invention.
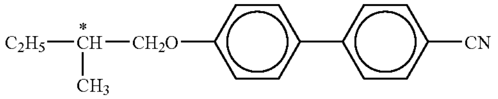
C 15
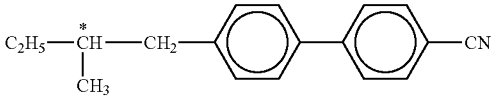
CB 15
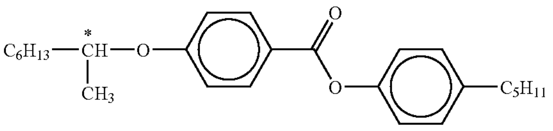
CM 21
TABLE C-continued
Table C shows possible dopants which are generally added to the mixtures according to the invention.
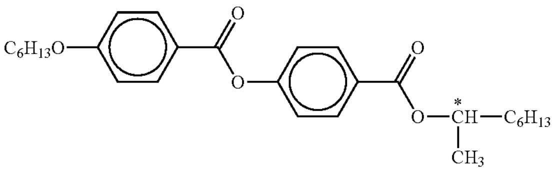
R/S-811
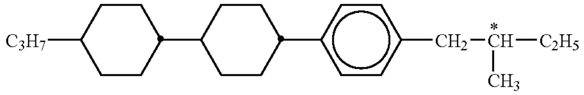
CM 44
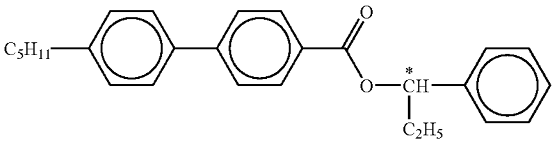
CM 45

TABLE C-continued

| Table C shows possible dopants which are generally added to the mixtures according to the invention. |
|---|
| 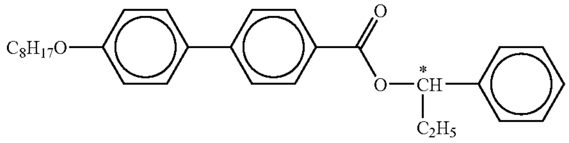<br>CM 47 |
| 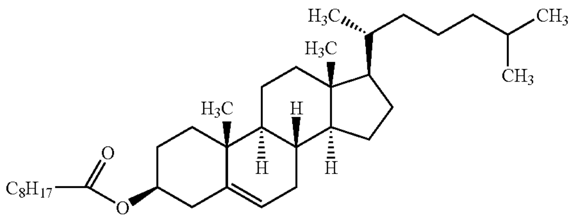<br>CN |

TABLE C-continued

| Table C shows possible dopants which are generally added to the mixtures according to the invention. |
|---|
| 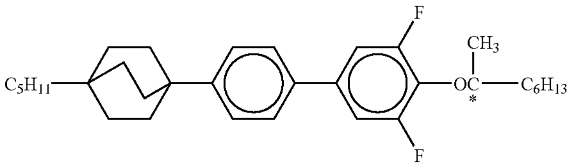<br>R/S-4011 |
| 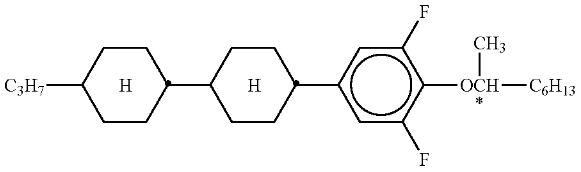<br>R/S-2011 |

TABLE D

| Stabilisers which can be added, for example, to the mixtures according to the invention are mentioned below. |
|---|
| 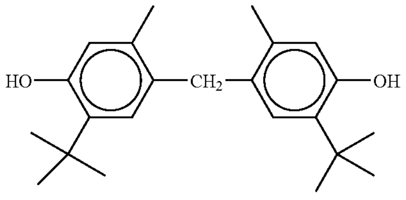 |
| 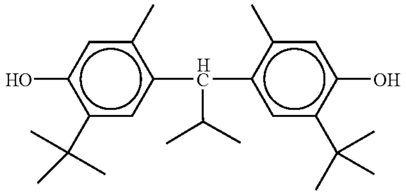 |
| 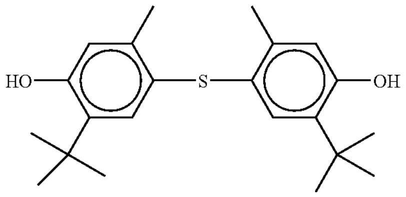 |
| 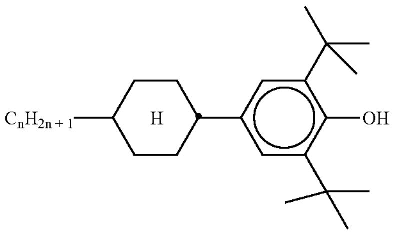 |

TABLE D-continued
| Stabilisers which can be added, for example, to the mixtures according to the invention are mentioned below. |
|---|
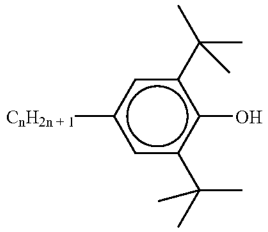
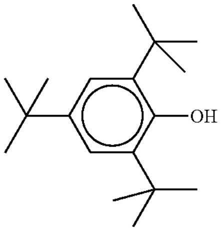
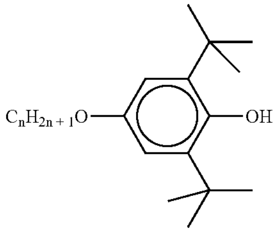
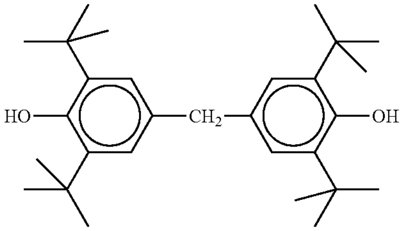
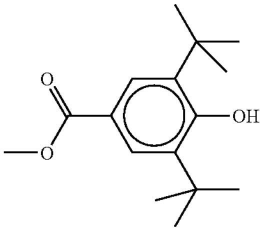
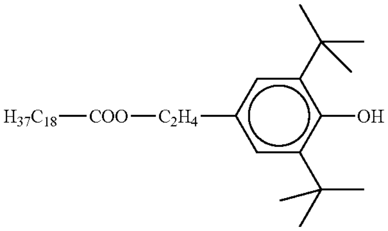

TABLE D-continued
| Stabilisers which can be added, for example, to the mixtures according to the invention are mentioned below. |
|---|
| 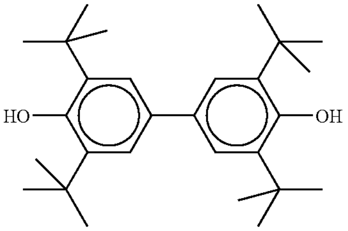 |
| 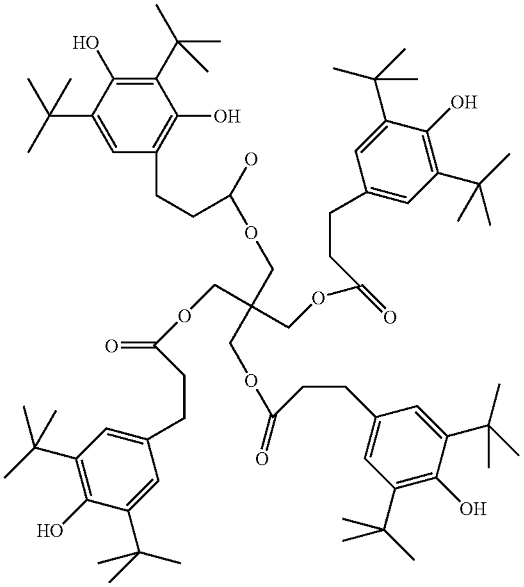 |
| 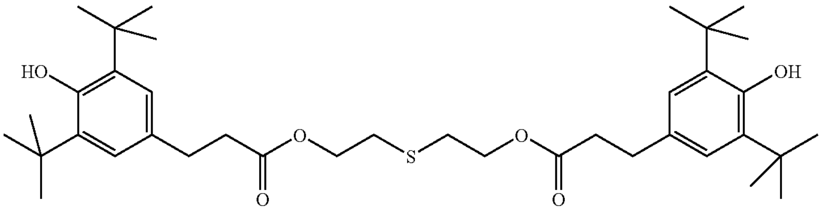 |
| 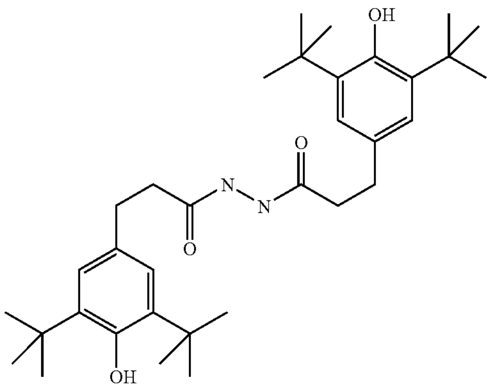 |

TABLE D-continued
| Stabilisers which can be added, for example, to the mixtures according to the invention are mentioned below. |
| --- |
| 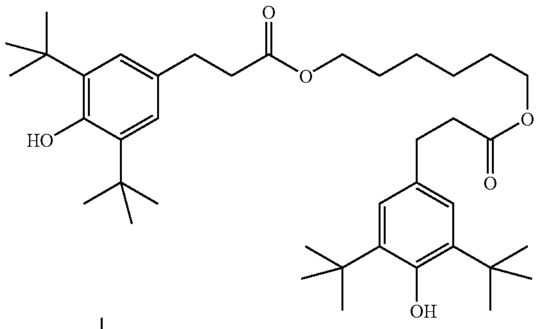 |
| 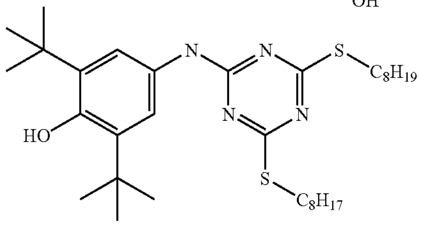 |
| 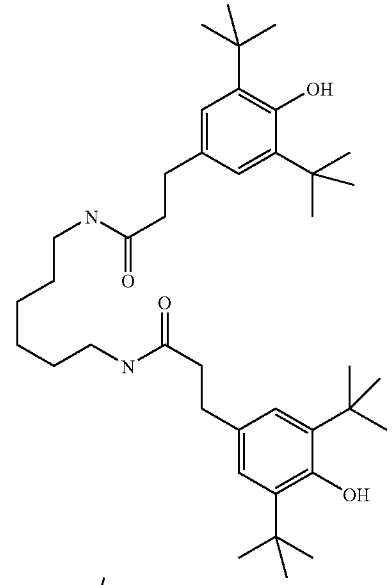 |
| 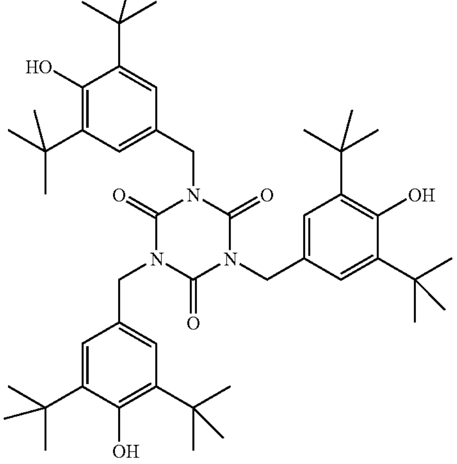 |

TABLE D-continued
Stabilisers which can be added, for example, to the mixtures according to the invention are mentioned below.
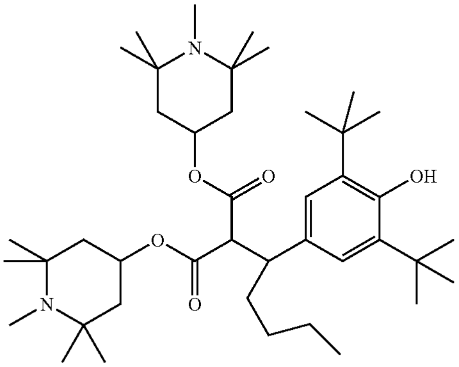
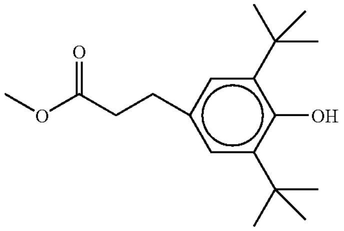
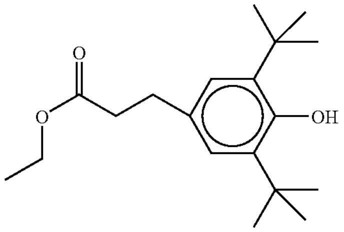
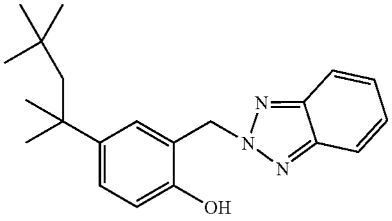
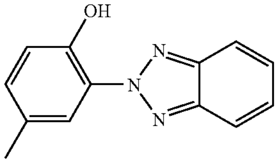
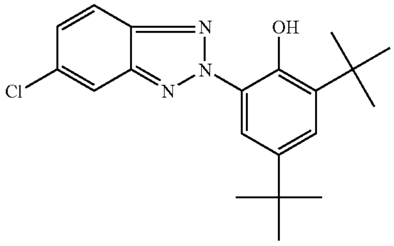

TABLE D-continued
| Stabilisers which can be added, for example, to the mixtures according to the invention are mentioned below. |
| --- |
| 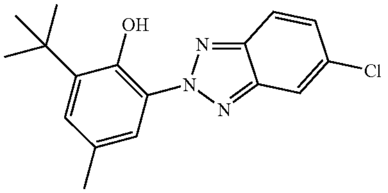 |
| 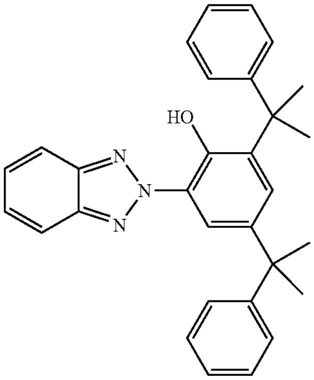 |
| 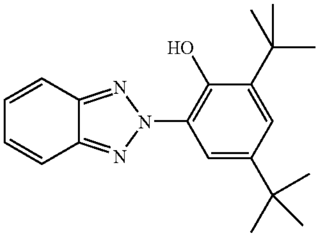 |
| 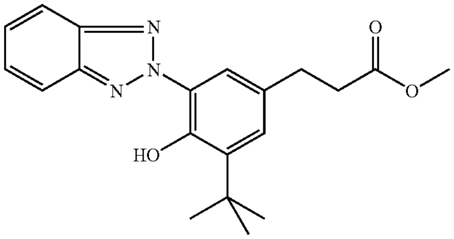 |
| 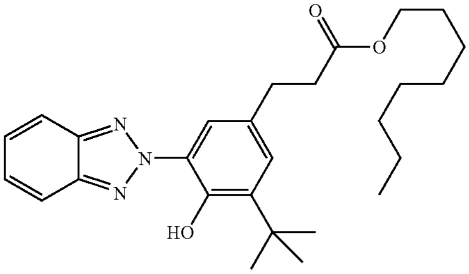 |

TABLE D-continued
| Stabilisers which can be added, for example, to the mixtures according to the invention are mentioned below. |
| --- |
| 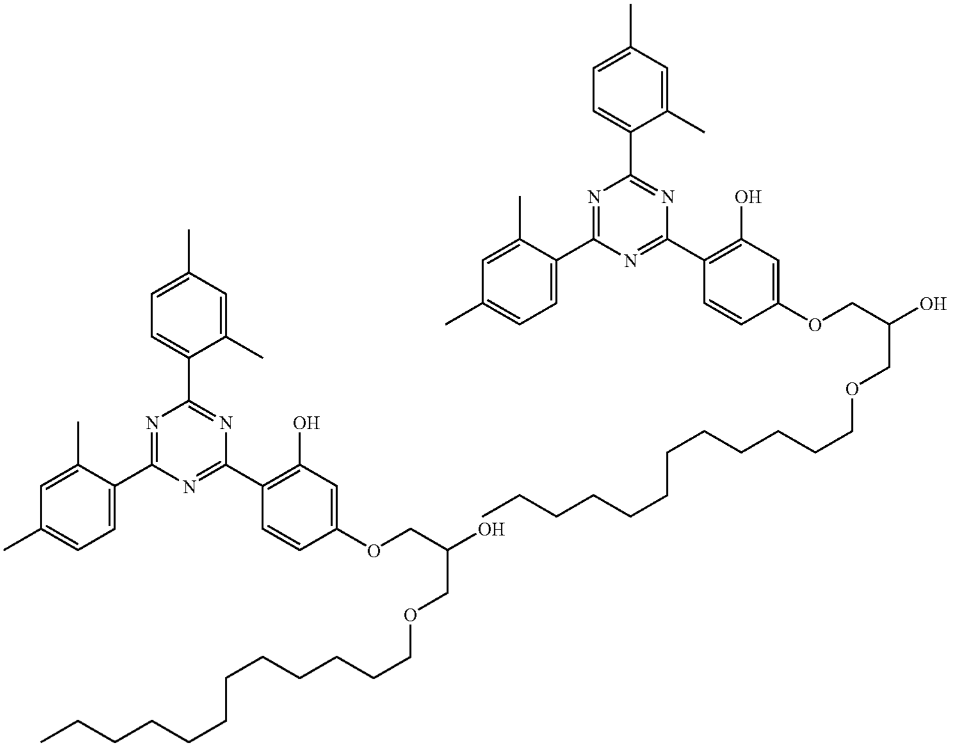 |
| 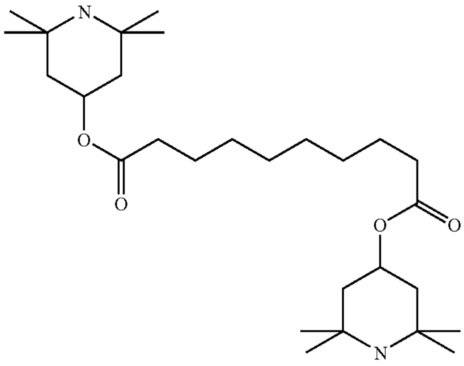 |
| 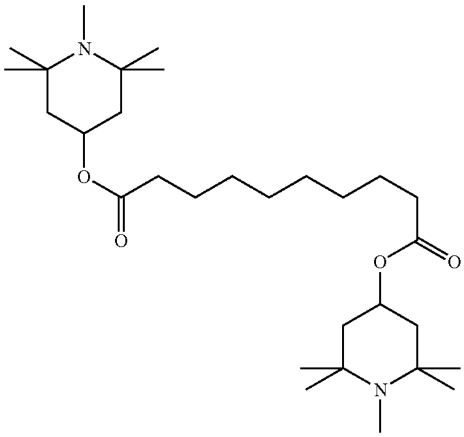 |

The following examples are intended to explain the invention without restricting it. Above and below, percentages are per cent by weight. All temperatures are given in degrees Celsius. m.p. denotes melting point, cl.p. denotes clearing point. Furthermore, C=crystalline state, N=nematic phase, S=smectic phase and I=isotropic phase. The data between these symbols represent the transition temperatures. Δn denotes optical anisotropy (589 nm, 20° C.), the flow viscosity $\nu_{20}$ ((mm$^2$/sec) was determined at 20° C. The rotational viscosity $\gamma_1$ [mPa·s] was likewise determined at 20° C.

"Conventional work-up" means that water is added if necessary, the mixture is extracted with dichoromethane, diethyl ether, methyl tert-butyl ether or toluene, the phases are separated, the organic phase is dried and evaporated, and the product is purified by distillation under reduced pressure or crystallisation and/or chromatography. The following abbreviations are used:

| | |
|---|---|
| n-BuLi | 1.6 molar solution of n-butyllithium in n-hexane |
| DMAP | 4-(dimethylamino)pyridine |
| THF | tetrahydrofuran |
| DCC | N,N'-dicyclohexylcarbodiimide |
| LDA | lithium dimethylamide |

Example 1

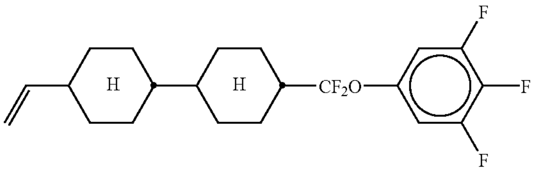

Step 1.1

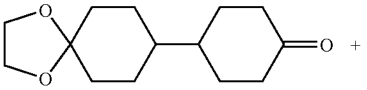

A

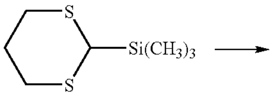

B

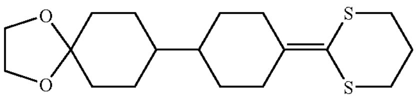

C 0.780 mol of B in 2.5 l of abs. THF are initially introduced and cooled to −70° C. At −70° C., 0.780 mol of n-BuLi (15% solution in n-hexane) is added dropwise, and the mixture is stirred at −70° C. for 0.5 hour and warmed slowly to −15° C. After 0.78 mol of A has been added at −70° C., the mixture is stirred overnight at room temperature. Methyl tert-butyl ether and $NaHCO_3$ solution are added to the mixture, which is subjected to conventional work-up. The crude product is recrystallised from n-heptane.

Step 1.2

D

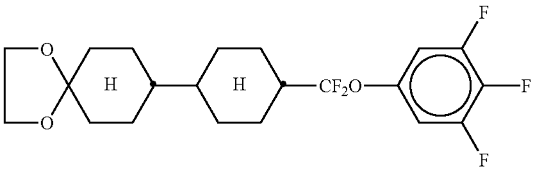

0.1 mol of C is dissolved in 300 ml of dichloromethane, and 0.1 mol of trifluoromethanesulfonic acid is added with ice cooling. The reaction mixture is stirred at 5° C., allowed to warm to room temperature and stirred for a further 2 hours. A mixture of 0.15 mol of 3,4,5-trifluorophenol and 0.18 mol of triethylamine in 30 ml of dichloromethane is added dropwise to the reaction mixture at −70° C., and the mixture is subsequently stirred at −70° C. for 1 hour. After 0.5 mol of triethylamine trishydrofluoride has been added, a mixture of 1,3-dibromo-5,5-dimethylhydantoin in 170 ml of dichloromethane is added in portions. The mixture is stirred at −70° C. for a further 1 hour, and 300 ml of a 1 molar NaOH solution are added at −20° C. The aqueous phase is separated off and extracted with dichloromethane. The combined organic phases are subjected to conventional work-up.

Step 1.3

E

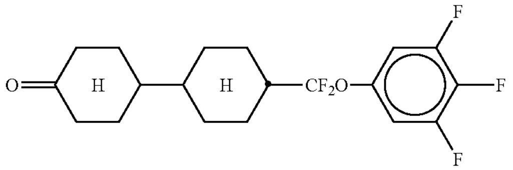

200 ml of formic acid are added to 0.083 mol of D dissolved in 250 ml of abs. toluene, and the mixture is stirred overnight at room temperature. The formic acid is separated off and extracted with toluene. The combined organic phases are subjected to conventional work-up. The residue is recrystallised from n-heptane.

F

Step 1.4

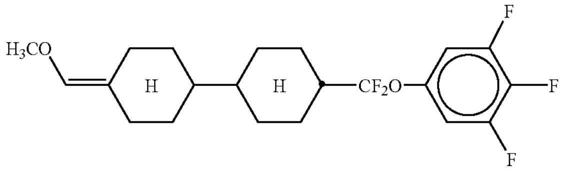

0.013 mol of E and 0.019 mol of methoxymethyltriphenylphosphonium chloride in 300 ml of abs. THF are introduced into an inert apparatus and cooled at −5° C. After 0.019 mol of potassium tert-butoxide in 50 ml of abs. THF has been added, the mixture is stirred at 0° C. for 1 hour and at room temperature overnight. After $H_2O$ and a few drops of dilute HCl have been added, the organic phase is separated off and subjected to conventional work-up.

Step 1.5

G

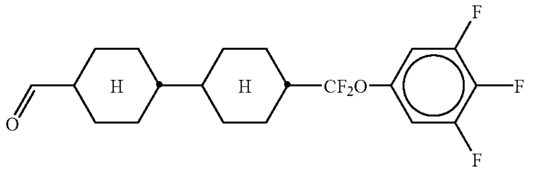

200 ml of formic acid are added to 0.083 mol of F dissolved in 250 ml of abs. toluene, and the mixture is stirred overnight at room temperature. The formic acid is separated off and extracted with toluene. The combined organic phases are subjected to conventional work-up. The residue is recrystallised from n-heptane.

Step 1.6

H

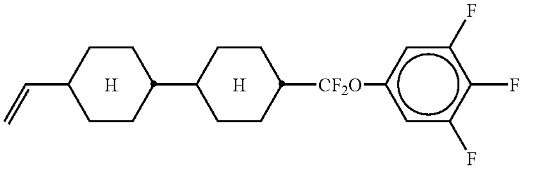

2.82 mmol of G and 3.36 mmol of methyltriphenylphosphonium bromide are dissolved in 40 ml of abs. THF and cooled to 2° C. 3.36 mmol of potassium tert-butoxide in 20 ml of abs. THF are added dropwise to this solution and dissolved overnight at room temperature. The triphenylphosphine oxide is filtered off with suction, and the filtrate is evaporated to dryness. The crude product, dissolved in n-heptane, is filtered through a silica frit, and the filtrate is re-evaporated. The residue is recrystallised from n-pentane at −20° C. C, 29; N, 88.4; I; Δn=0.0761; Δε=8.3.

The following compounds of the formula

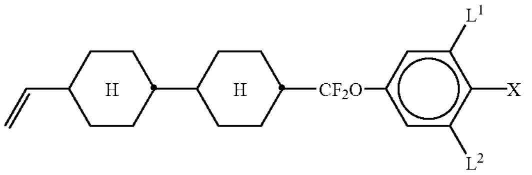

are prepared analogously:

| X | $L^1$ | $L^2$ |
|---|---|---|
| F | H | H |
| F | F | H |
| $OCF_3$ | H | H |
| $OCF_3$ | F | H |
| $OCF_3$ | F | F |
| $OCH_2CF_3$ | H | H |
| $OCH_2CF_3$ | F | H |

-continued

| X | $L^1$ | $L^2$ |
|---|---|---|
| $OCH_2CF_3$ | F | F |
| Cl | H | H |
| Cl | F | H |
| Cl | F | F |
| CN | H | H |
| CN | F | H |
| CN | F | F |
| $SF_5$ | H | H |
| $SF_5$ | F | H |
| $SF_5$ | F | F |
| NCS | H | H |
| NCS | F | H |
| NCS | F | F |
| $OCHF_2$ | H | H |
| $OCHF_2$ | F | H |
| $OOHF_2$ | F | F |
| $CF_3$ | H | H |
| $CF_3$ | F | H |
| $CF_3$ | F | F |
| $OCF_2CHFCF_3$ | H | H |
| $OCF_2CHFCF_3$ | F | H |
| $OCF_2CHFCF_3$ | F | F |
| $OC_3F_7$ | H | H |
| $OC_3F_7$ | F | H |
| $OC_3F_7$ | F | F |
| $C_3F_7$ | H | H |
| $C_3F_7$ | F | H |
| $C_3F_7$ | F | F |

Mixture Examples

Example M1

| | | | |
|---|---|---|---|
| BCH-3F.F | 10.80% | Clearing point [° C.]: | 90.3 |
| BCH-5F.F | 9.00% | Δn [589 nm, 20° C.]: | 0.0945 |
| $ECCP-3OCF_3$ | 4.50% | Δε [1 kHz, 20° C.]: | 5.6 |
| $ECCP-5OCF_3$ | 4.50% | | |
| CBC-33F | 1.80% | | |
| CBC-53F | 1.80% | | |
| CBC-55F | 1.80% | | |
| PCH-6F | 7.20% | | |
| PCH-7F | 5.40% | | |
| $CCP-2OCF_3$ | 7.20% | | |
| $CCP-3OCF_3$ | 10.80% | | |
| $CCP-4OCF_3$ | 6.30% | | |
| $CCP-5OCF_3$ | 9.90% | | |
| PCH-5F | 9.00% | | |
| CCQU-V-F | 10.00% | | |

Example M2

| | | | |
|---|---|---|---|
| CCP-2F.F.F | 12.00% | Clearing point [° C.]: | 76 |
| CCP-3F.F.F | 10.00% | Δn [589 nm, 20° C.]: | 0.0916 |
| CCP-5F.F.F | 1.00% | $V_{10,0,20}$: | 1.23 |
| $CCP-2OCF_3$ | 8.00% | $\gamma_1$: | 152 |
| $CCP-3OCF_3$ | 8.00% | | |
| $CCP-4OCF_3$ | 7.00% | | |
| $CCP-5OCF_3$ | 7.00% | | |
| CGU-2-F | 12.00% | | |
| CGU-3-F | 10.00% | | |
| CGU-5-F | 10.00% | | |
| CCQU-V-F | 15.00% | | |

Example M3

| | | | |
|---|---|---|---|
| CCP-2F.F.F | 12.00% | Clearing point [° C.]: | 75.7 |
| CCP-3F.F.F | 10.00% | Δn [589 nm, 20° C.]: | 0.0928 |
| CCP-5F.F.F | 6.00% | $V_{10,0,20}$: | 1.18 |
| CCP-2OCF$_2$.F.F | 1.00% | $\gamma_1$: | 146 |
| CCP-2OCF$_3$ | 8.00% | | |
| CCP-3OCF$_3$ | 8.00% | | |
| CCP-4OCF$_3$ | 7.00% | | |
| CGU-2-F | 12.00% | | |
| CGU-3-F | 10.00% | | |
| CWCQU-2-F | 5.50% | | |
| PGU-2-F | 5.50% | | |
| CCQU-V-F | 15.00% | | |

Example M4

| | | | |
|---|---|---|---|
| CCP-2F.F.F | 12.00% | Clearing point [° C.]: | 75 |
| CCP-3F.F.F | 10.00% | Δn [589 nm, 20° C.]: | 0.0932 |
| CCP-2OCF$_3$ | 8.00% | $V_{10,0,20}$: | 1.17 |
| CCP-3OCF$_3$ | 8.00% | $\gamma_1$: | 139 |
| CCP-4OCF$_3$ | 7.00% | | |
| CCP-5OCF$_3$ | 4.00% | | |
| CGU-2-F | 12.00% | | |
| CGU-3-F | 4.00% | | |
| CCQU-2-F | 12.00% | | |
| PGU-2-F | 8.00% | | |
| CCQU-V-F | 15.00% | | |

Example M5

| | | | |
|---|---|---|---|
| CCP-2F.F.F | 12.00% | Clearing point [° C.]: | 76 |
| CCP-3F.F.F | 2.50% | Δn [589 nm, 20° C.]: | 0.0930 |
| CCP-2OCF$_3$ | 8.00% | $V_{10,20}$: | 1.20 |
| CCP-3OCF$_3$ | 8.00% | $\gamma_1$: | 137 |
| CCP-4OCF$_3$ | 7.00% | | |
| CCP-5OCF$_3$ | 3.00% | | |
| CGU-2-F | 12.00% | | |
| CGU-3-F | 10.00% | | |
| CCP-2F.F | 9.00% | | |
| CCP-3F.F | 6.00% | | |
| PGU-2-F | 6.50% | | |
| CCGU-3-F | 1.00% | | |
| CCQU-V-F | 15.00% | | |

Example M6

| | | | |
|---|---|---|---|
| BCH-3F.F | 10.80% | Clearing point [° C.]: | 81.7 |
| BCH-5F.F | 9.00% | Δn [589 nm, 20° C.]: | 0.0996 |
| ECCP-3OCF$_3$ | 4.50% | Δε [1 kHz, 20° C.]: | 6.5 |
| ECCP-5OCF$_3$ | 4.50% | d*Δn [nm]: | 0.5 |
| CBC-33F | 1.80% | Twist: | 90 |
| CBC-53F | 1.80% | | |
| CBC-55F | 1.80% | | |
| PCH-6F | 7.20% | | |
| PCH-7F | 5.40% | | |
| CCP-2OCF$_3$ | 7.20% | | |
| CCP-3OCF$_3$ | 10.80% | | |
| CCP-4OCF$_3$ | 6.30% | | |
| CCP-5OCF$_3$ | 9.90% | | |
| PCH-5F | 9.00% | | |
| PUQU-V2-F | 10.00% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A liquid-crystalline medium comprising at least two mesogenic compounds:

wherein the medium contains substantially no compounds having a cyano group; wherein at least one mesogenic compound is a compound of the formula I

I

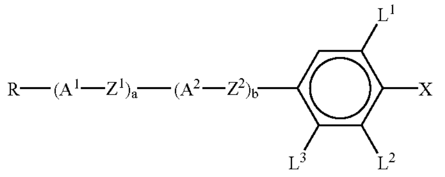

in which

R is vinyl, $CH_3CH{=}CH$—, $CH_2{=}CHCH_2CH_2$— or $CH_3CH{=}CHCH_2CH_2$—, $A^1$ and $A^2$ are each, independently of one another, a) a 1,4-cyclohexenylene or 1,4-cyclohexylene radical, in which one or two non-adjacent $CH_2$ groups are optionally replaced by —O— or —S—, b) a 1,4-phenylene radical, in which one or two CH groups are optionally replaced by N, c) a radical selected from the group consisting of piperidine-1,4-diyl, 1,4-bicyclo[2.2.2]octylene, phenanthrene-2,7-diyl, naphthalene-2,6-diyl, decahydronaphthalene-2,6-diyl, 1,2,3,4-tetrahydronaphthalene-2,6-diyl, phenanthrene-2,7-diyl and fluorene-2,7-diyl, where the radicals a), b) and c) are optionally mono-to perhalo-substituted by halogen atoms, X is F, Cl, NCS, $SF_5$, or a halogenated or unsubstituted alkyl, alkoxy, alkenyloxy or alkenyl radical having 1 to 5 carbon atoms, $Z^1$ and $Z^2$ are each, independently of one another, —CO—O—, —O—CO—, —$CF_2O$—, —$OCF_2$—, —$CH_2O$—, —$OCH_2$—, —$CH_2CH_2$—, —$(CH_2)_4$—, —$C_2F_4$—, —$CH_2CF_2$—, —$CF_2CH_2$—, —CF=CF—, —CH=CH—, —C≡C— or a single bond, a is 0, 1 or 2, b is 0, 1 or 2, provided that a and b are not both 0 and that the compound contains at least one bridge $Z^1$ or $Z^2$ which is —$CF_2O$— or —$OCF_2$—, and $L^1$, $L^2$ and $L^3$ are each, independently of one another, H, F, or Cl; and wherein at least one other mesogenic compound is a compound of one of formulae II to IX:

II

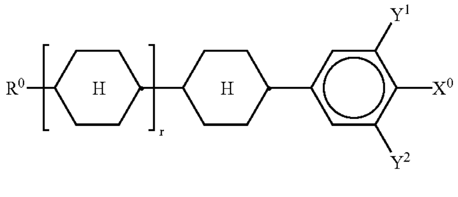

-continued

III

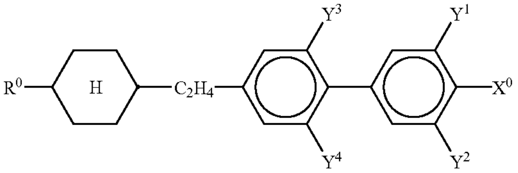

IV

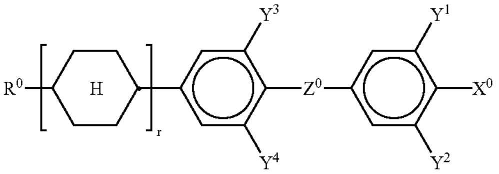

V

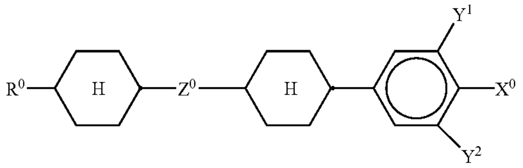

VI

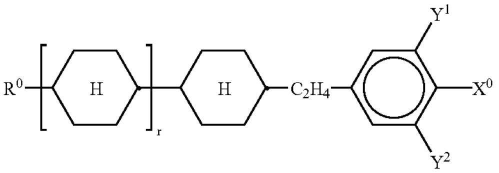

VII

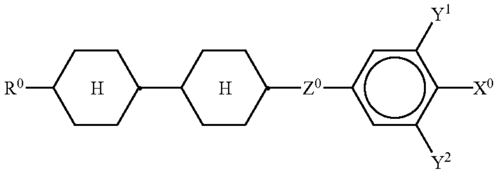

VIII

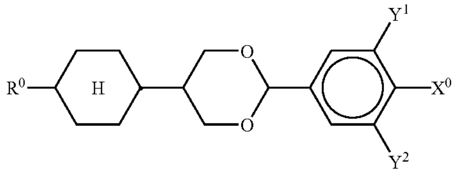

IX

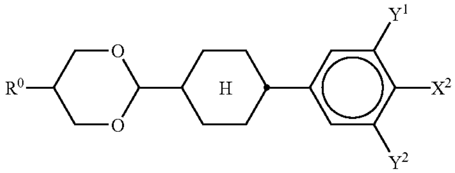

in which:

$R^0$ is n-alkyl, oxaalkyl, fluoroalkyl, alkenyloxy or alkenyl, each having 1 to 9 carbon atoms, $X^0$ is halogenated alkoxy having 1 to 7 carbon atoms, $Z^0$ is $—CH{=}CH—$, $—C_2H_4—$, $—(CH_2)_4—$, $—C_2F_4—$, $—CF{=}CF—$, $—CF_2O—$, $—OCF_2—$ or $—COO—$, $Y^1$, $Y^2$, $Y^3$ and $Y^4$ are each, independently of one another, H or F, and r is 0 or 1, provided that the variables are selected such that the compounds of formulae IV, V and VII do not include compounds within the scope of formula I; and provided that the medium does not contain:

a compound of the formula II

II

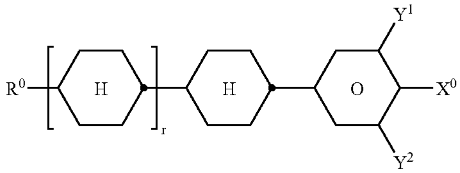

wherein $R^0$ is alkenyl and r is 1, a compound of the formula IV

IV

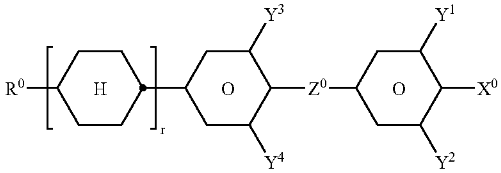

where $R^0$ is alkenyl, $Z^0$ is a single bond and r is 1, or a compound of any of formulae RI—RV or RIX—RX:

RI

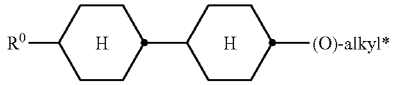

RII

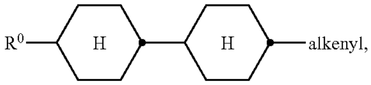

RIII

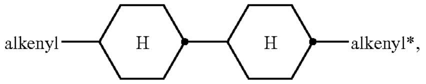

RIV

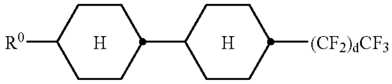

RV

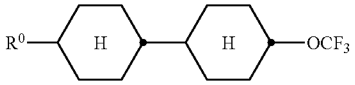

RIX

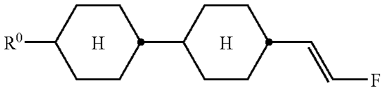

RX

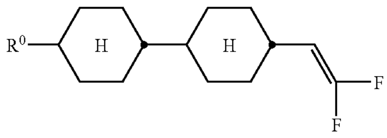

where $R^0$ is alkenyl alkyl* are each, independently of one another, a straight-chain or branched alkyl radical having 1-9 carbon atoms, alkenyl and alkenyl* are each, independently of one another, a straight-chain or branched alkenyl radical having up to 9 carbon atoms and d is 0, 1 or 2.

2. A liquid-crystalline medium according to claim 1, wherein in formula I, a+b=1 or a+b=2.

3. A liquid-crystalline medium according to claim 1, wherein in formula I, $L^1$ is fluorine and $L^2$ is fluorine or hydrogen.

4. A liquid-crystalline medium according to claim 1, wherein in formula I, $L^2$ and $L^3$ are fluorine.

5. A liquid-crystalline medium according to claim 1, wherein the compound of formula I is of one of the formulae I1 to I105:

I1

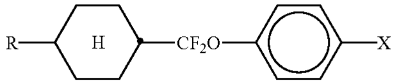

I2

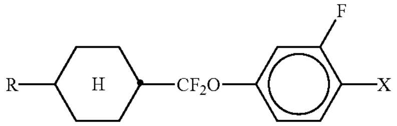

I3

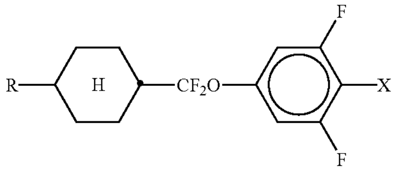

I4

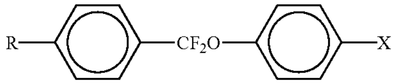

I5

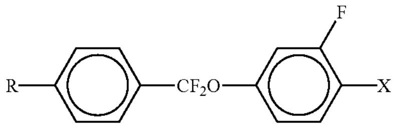

I6

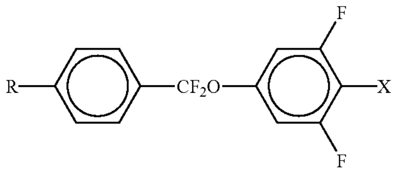

I7

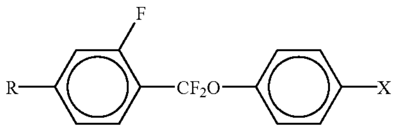

I8

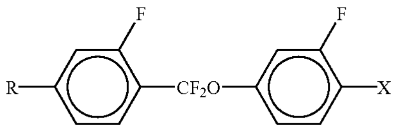

I9

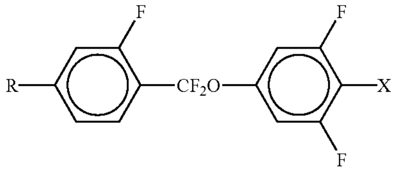

-continued

I10

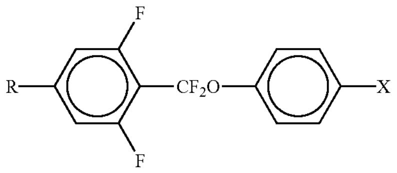

I11

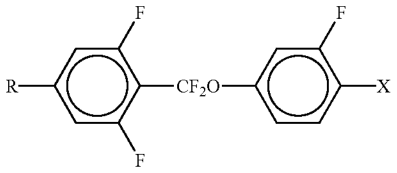

I12

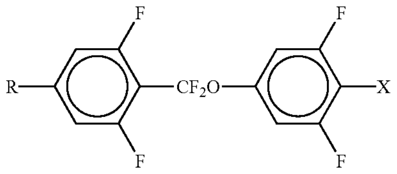

I13

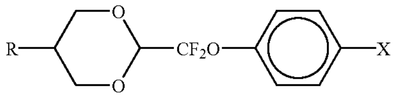

I14

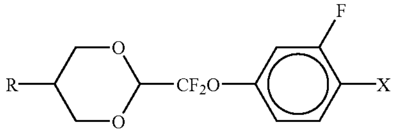

I15

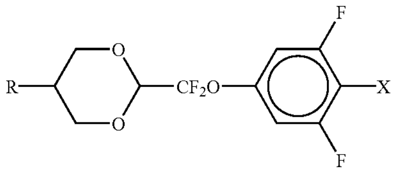

I16

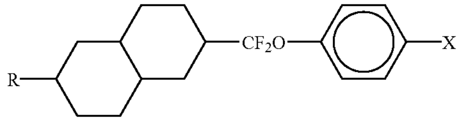

I17

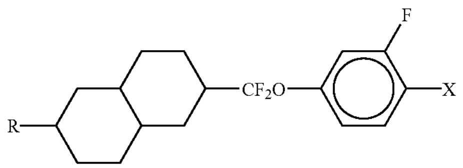

I18

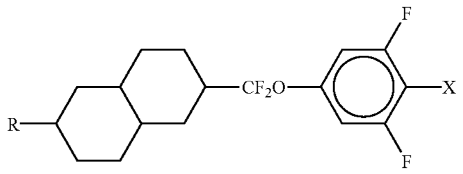

I19

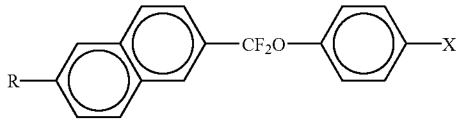

-continued
I20
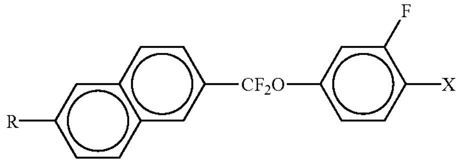
I21
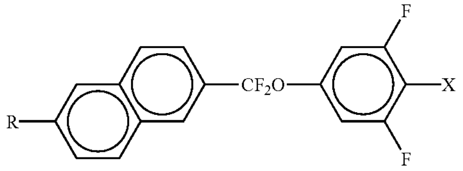
I22
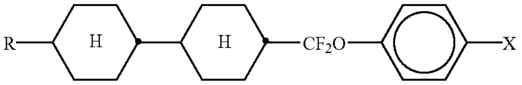
I23
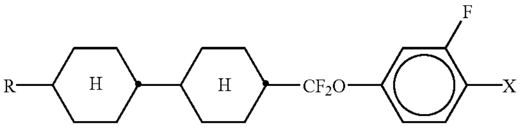
I24
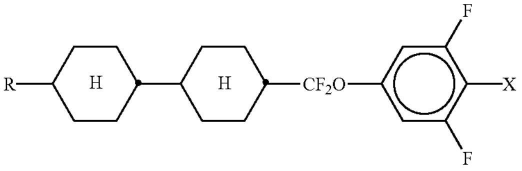
I25
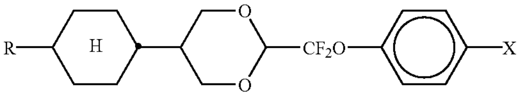
I26
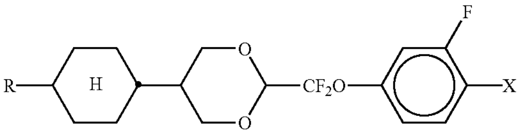
I27
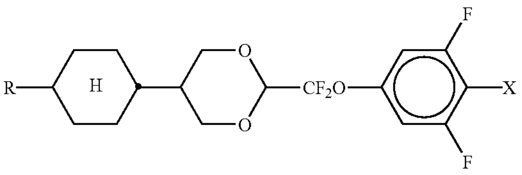
I28
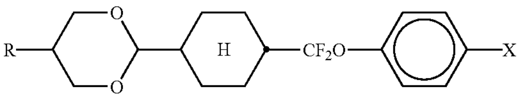
I29
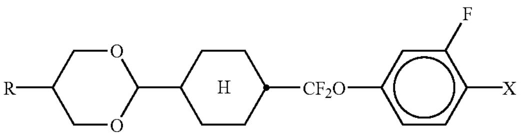
-continued
I30
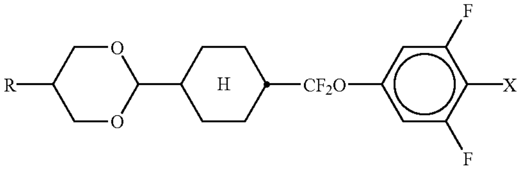
I31
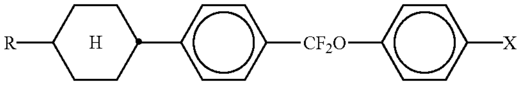
I32
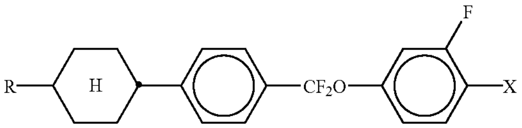
I33
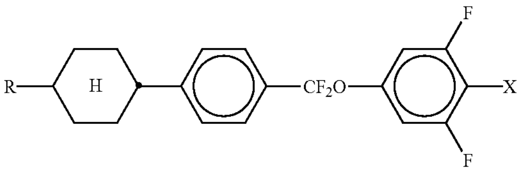
I34
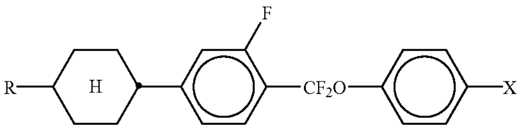
I35
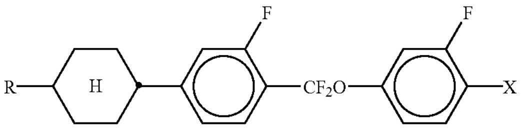
I36
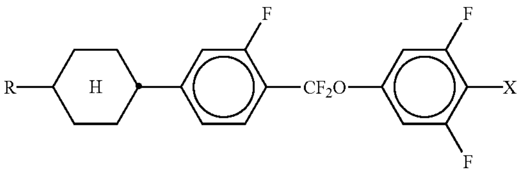
I37
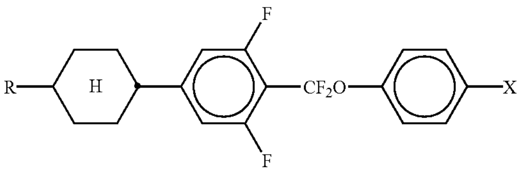
I38
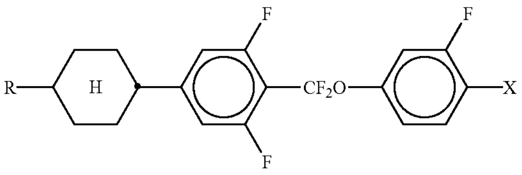

-continued
I39
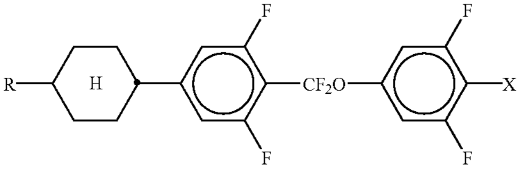
I40
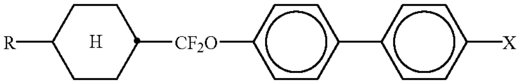
I41
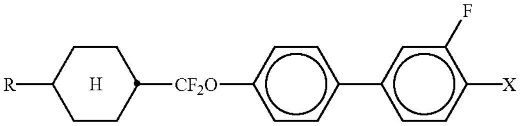
I42
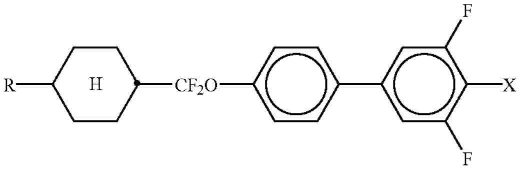
I43
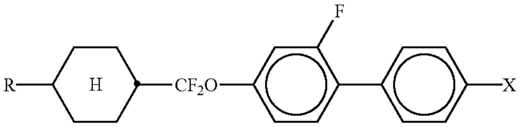
I44
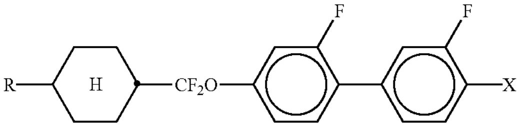
I45
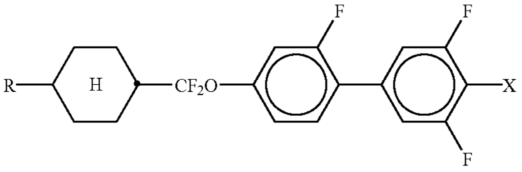
I46
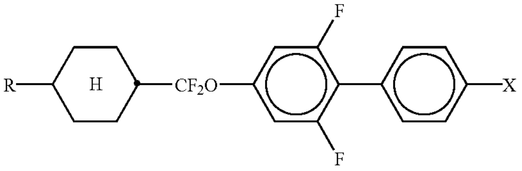
I47
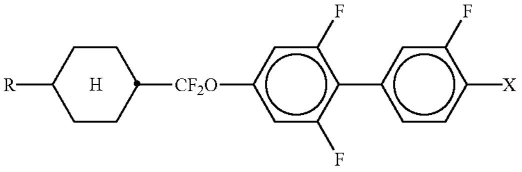
-continued
I48
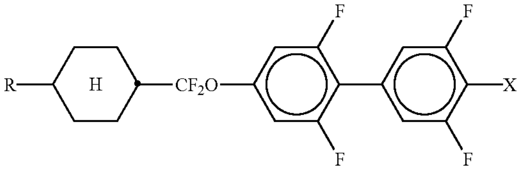
I49
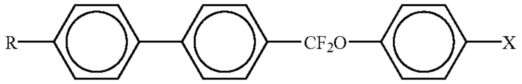
I50
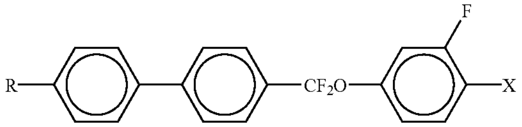
I51
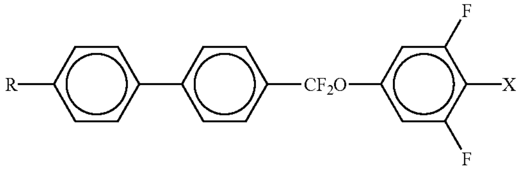
I52
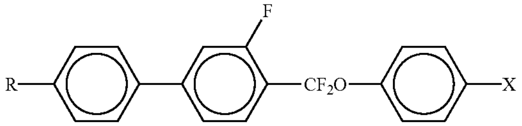
I53
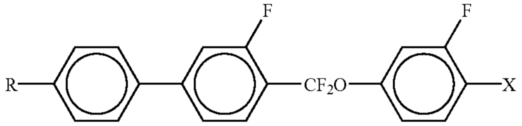
I54
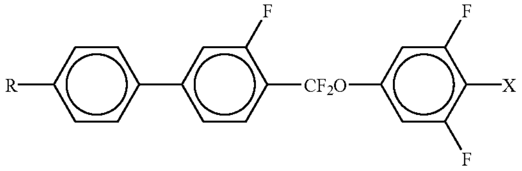
I55
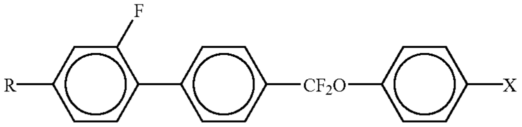
I56
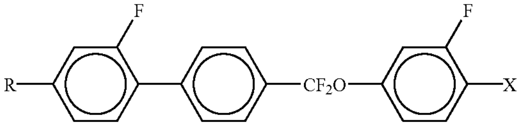

-continued
I57
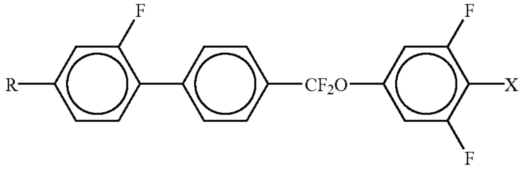
I58
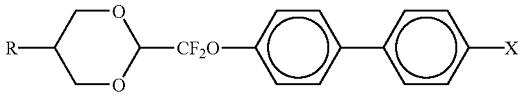
I59
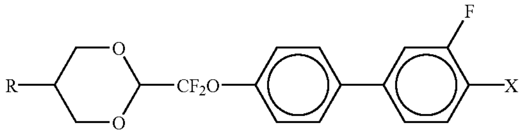
I60
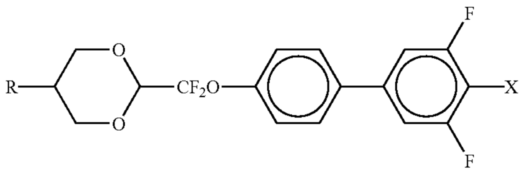
I61
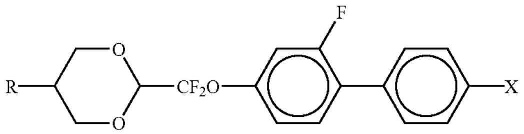
I62
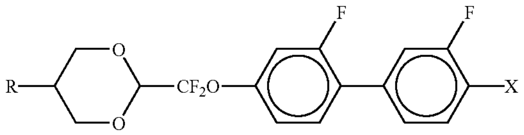
I63
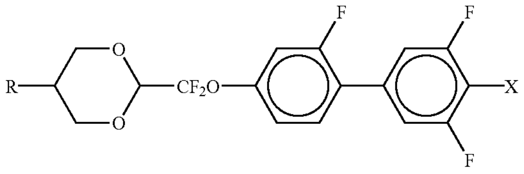
I64
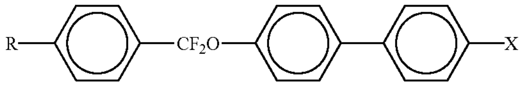
I65
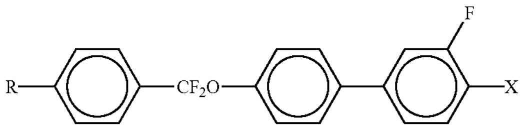
-continued
I66
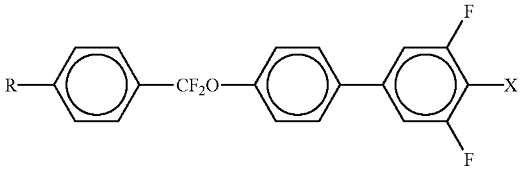
I67
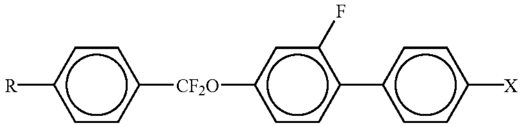
I68
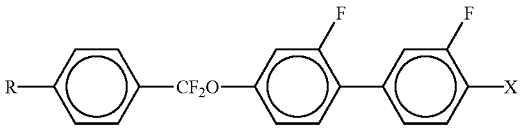
I69
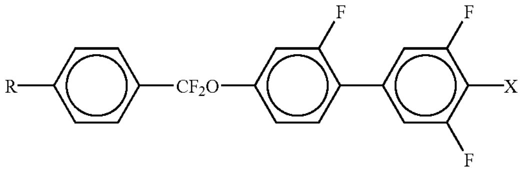
I70
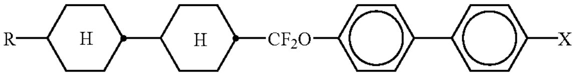
I71
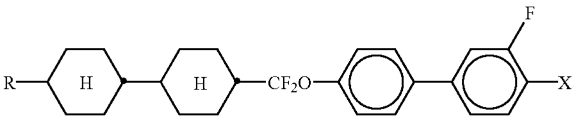
I72
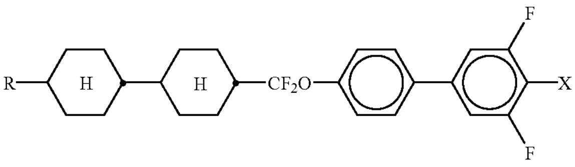
I73
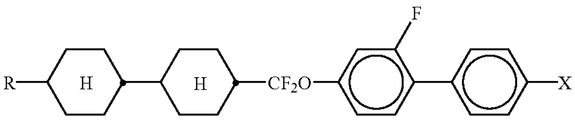
I74
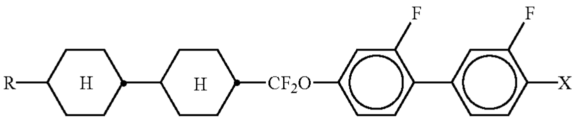

-continued
I75
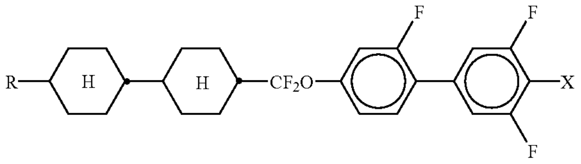
I76
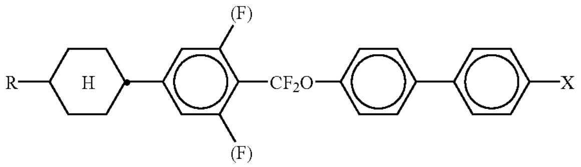
I77
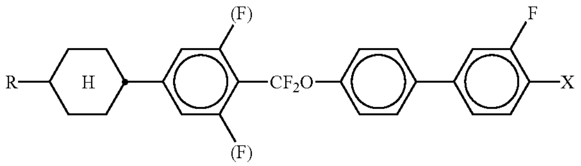
I78
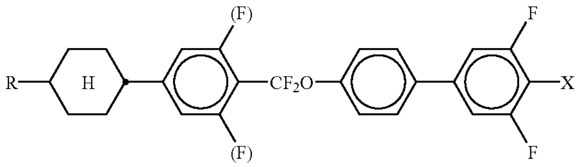
I79
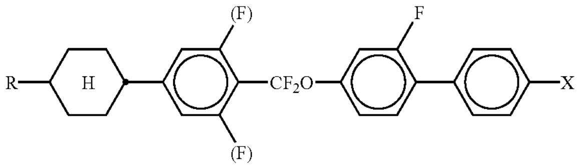
I80
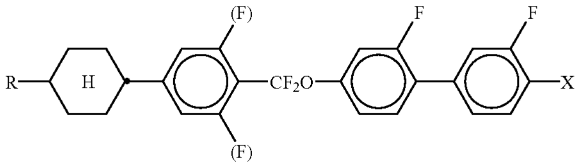
I81
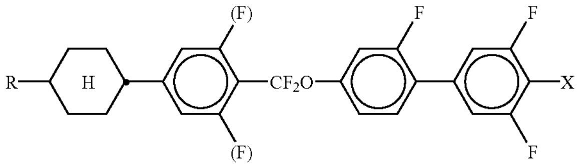
I82
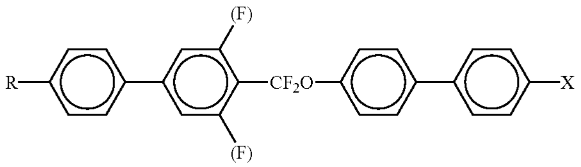
-continued
I83
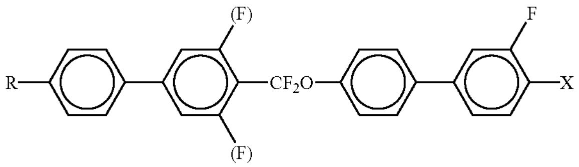
I84
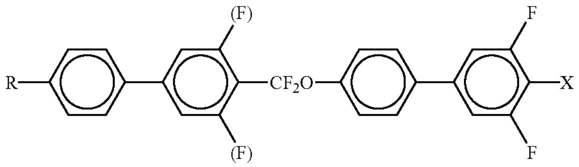
I85
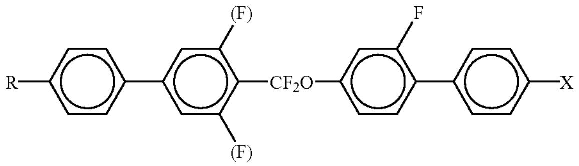
I86
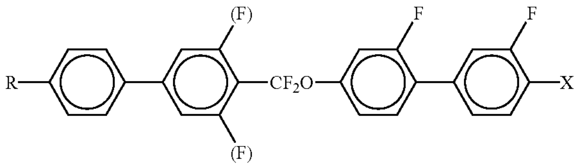
I87
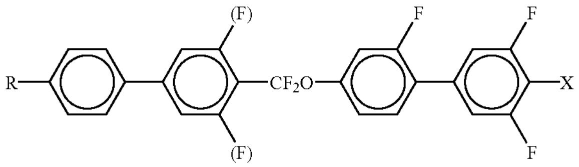
I88
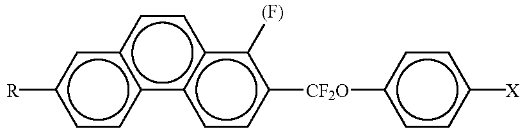
I89
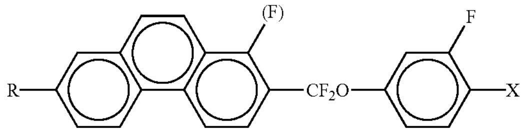
I90
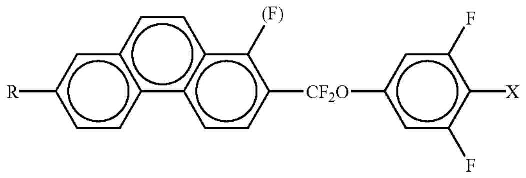

-continued

I91

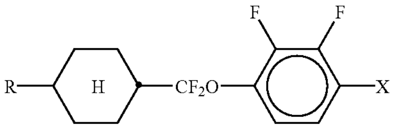

I92

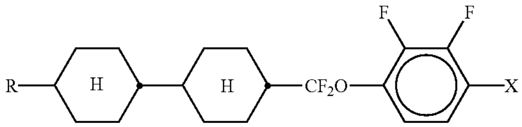

I93

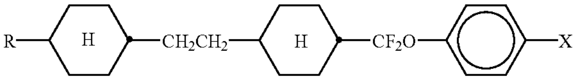

I94

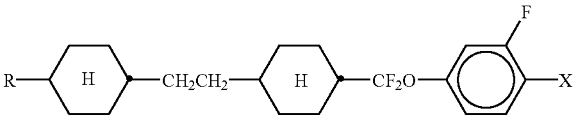

I95

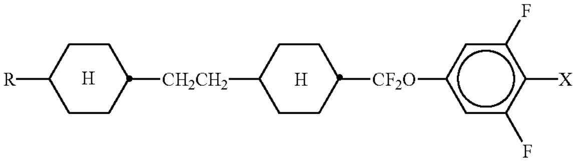

I96

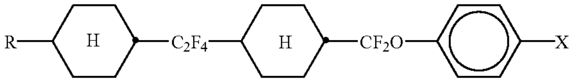

I97

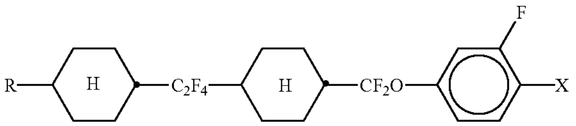

I98

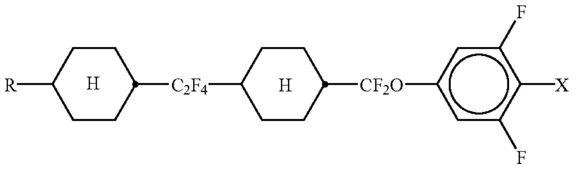

I99

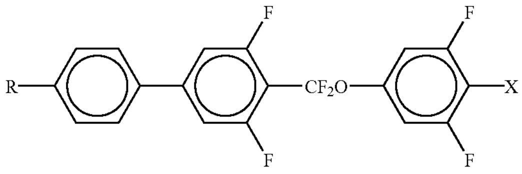

I100

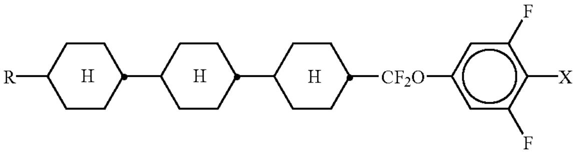

-continued

I101

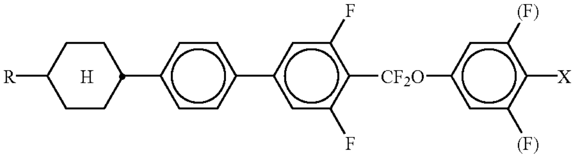

I102

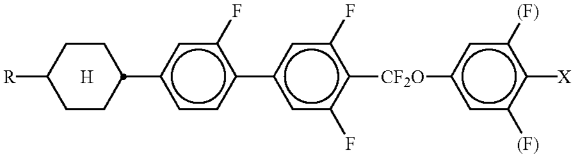

I103

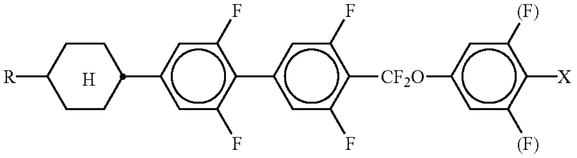

I104

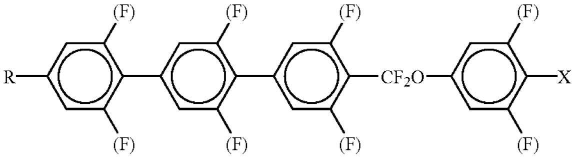

I105

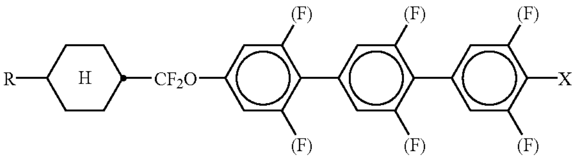

in which

R and X are as defined in claim 1 and (F) means fluorine or hydrogen.

6. An electro-optical liquid-crystal display which comprises a liquid-crystalline medium according to claim 1.

7. A medium of claim 1, wherein, in formula I, $A^1$ and $A^2$ are independently selected from Phe, PheF, PheFF, Cyc, Che, Pyr, Dio, Dec or Nap, provided that the compound does not contain more than one of Pyr, Dio, Dec, or Nap, where Cyc denotes a 1,4-cyclohexylene radical, Che denotes a 1,4-cyclohexenylene radical, Dio denotes a 1,3-dioxane-2,5-diyl radical, Phe denotes a 1,4-phenylene radical, Pyr denotes a pyrimidine-2,5-diyl radical, PheF denotes a 2- or 3-fluoro-1,4-phenylene radical, PheFF denotes a 2,3-difluoro- or 2,6-difluoro-1,4-phenylene radical, Nap denotes a substituted or unsubstituted naphthalene radical, and Dec denotes a decahydronaphthalene radical.

8. A medium of claim 1, wherein, in formula I, $A^1$ and $A^2$ are independently selected from monofluoro-substituted or difluoro-substituted 1,4-phenylene.

9. A liquid-crystalline medium of claim 1, wherein the medium has a nematic phase down to −20° C., a clearing point above 80° C., and a dielectric anisotropy, $\Delta\epsilon$, of $\geqq 4$.

10. A liquid-crystalline medium of claim 9, wherein the medium has a TN threshold below 1.5 V.

11. A liquid-crystalline medium of claim 1, wherein the medium contains 5-95% by weight of compounds of the formula I.

12. A liquid-crystalline medium of claim 1, wherein the medium contains 10-60% by weight of compounds of the formula I.

13. A liquid-crystalline medium of claim 1, wherein the medium comprises at least one compound of one of the formulae II to IX wherein $X^0$ is —$OCF_3$.

14. A liquid-crystalline medium of claim 1, wherein the medium comprises at least one compound of the formula II or III.

15. A liquid-crystalline medium of claim 1, wherein the medium has a clearing point above 75° C.

16. A liquid-crystalline medium of claim 1, wherein the medium has a flow viscosity, $\nu_{20}$, at 20° C., of <60 $mm^2 \cdot s^{-1}$.

17. A liquid-crystalline medium of claim 1, wherein the medium has a rotational viscosity, $\gamma_1$, at 20° C., of 152 mPa·s or less.

* * * * *